US008303974B2

(12) United States Patent
Macdonald et al.

(10) Patent No.: US 8,303,974 B2
(45) Date of Patent: Nov. 6, 2012

(54) DRUG DELIVERY SYSTEM FOR THE PREVENTION OF CEREBRAL VASOSPASM

(75) Inventors: R. Loch Macdonald, Toronto (CA); Brian Leuthner, Summit, NJ (US)

(73) Assignee: Edge Therapeutics, Inc., New Providence, NJ (US)

( * ) Notice: Subject to any disclaimer, the term of this patent is extended or adjusted under 35 U.S.C. 154(b) by 452 days.

(21) Appl. No.: 12/137,320

(22) Filed: Jun. 11, 2008

(65) Prior Publication Data
US 2008/0305147 A1   Dec. 11, 2008

Related U.S. Application Data

(60) Provisional application No. 60/943,124, filed on Jun. 11, 2007, provisional application No. 60/976,902, filed on Oct. 29, 2007.

(51) Int. Cl.
*A61K 9/10* (2006.01)
(52) U.S. Cl. ......................... 424/423; 424/422
(58) Field of Classification Search .................. None
See application file for complete search history.

(56) References Cited

U.S. PATENT DOCUMENTS

| 5,650,489 | A |   | 7/1997 | Lam et al. |
| 5,712,171 | A |   | 1/1998 | Zambias et al. |
| 5,993,855 | A | * | 11/1999 | Yoshimoto et al. ............ 424/489 |
| 6,123,956 | A |   | 9/2000 | Baker et al. |
| 2006/0205733 | A1 |   | 9/2006 | Dixon et al. |
| 2006/0217340 | A1 |   | 9/2006 | Braydon et al. |
| 2006/0229269 | A1 | * | 10/2006 | Wellman et al. ................. 514/44 |

FOREIGN PATENT DOCUMENTS

| WO | 95/18972 | 7/1995 |
| WO | 96/22529 | 7/1996 |
| WO | 2006/084005 | 8/2006 |

OTHER PUBLICATIONS http://www.brain-aneurysm.com/cv.html.*
Barth et al. "Effect of Nicardipine Prolonged Release Implant on Cerebral Vasospasm and Clinical Outcome After Severe Aneurysmal Subarachnoid Hemorrhage" Stoke 2007,38:330-336 published online Dec. 2006.*
Kasuya et al. "Efficacy and Safety of Nicardipine Prolonged-Release Implants for Preventing Vasospasm in Humans". Stroke 2002; 33: 1011-1015.*
Pradilla et al. "Pharmacokinetics of controlled-release polymers in the subarachnoid space after subarachnoid hemorrhage in rabbits" J. Neurosurg. Jul. 2004; 101(1) (abstract).*
Llinas, R. et al., "Electrophysiological properties of in vitro Purkinje cell somata in mammalian cerebellar slices", J. Physiol., Aug. 1980, vol. 305, pp. 171-195.

(Continued)

*Primary Examiner* — Robert A. Wax
*Assistant Examiner* — Danah Al-Awadi
(74) *Attorney, Agent, or Firm* — Beverly W. Lubit; Greenberg Traurig, LLP

(57) ABSTRACT

The present invention relates to the treatment and prevention of vasospasm. The present invention provides a system for treating a cerebral vasospasm in a human utilizing a pharmaceutical composition and administrating a therapeutically effective amount of the pharmaceutical composition to a predetermined location in close proximity to a cerebral artery within a subarachnoid space wherein the pharmaceutical composition produces a localized pharmacologic effect thereby treating the cerebral vasospasm.

37 Claims, 2 Drawing Sheets

OTHER PUBLICATIONS

Yan, L. et al., "The spider toxin omega-Aga IIIA defines a high affinity site on neuronal high voltage-activated calcium channels", J. Biol. Chem., Jul. 14, 2000, vol. 275, No. 28, pp. 21309-21316.

Newcomb, R. et al., "Selective peptide antagonist of the class E calcium channel from the venom of the tarantula *Hysterocrates gigas*", Biochemistry, Nov. 3, 1998, vol. 37, No. 44, pp. 15353-15362.

Tottene, A. et al., "Alpha(1E) subunits form the pore of three cerebellar R-type calcium channels with different pharmacological and permeation properties", J. Neurosci., Jan. 1, 2000, vol. 20, No. 1, pp. 171-178.

Wang, G. et al., "An R-type Ca(2+) current in neurohypophysial terminals preferentially regulates oxytocin secretion", J. Neuroscience, Nov. 1, 1999, vol. 19, No. 21, pp. 9235-9241.

Coplin, W. M. et al., "Cerebrospinal fluid creatine kinase-BB isoenzyme activity and outcome after subarachnoid hemorrhage", Arch. Neurol., Nov. 1999, vol. 56, No. 11, pp. 1348-1352.

Langer, R., "New methods of drug delivery", Science, Sep. 28, 1990, vol. 248, No. 4976, pp. 1527-1533.

Sawhney, A.S. et al., "Bioerodible hydrogels based on photopolymerized poly(ethylene glycol)-co-poly(.alpha.-hydroxy acid) diacrylate macromers", Macromolecules, 1993, vol. 26, No. 4, pp. 581-587.

Llinas, R. et al., Blocking and isolation of a calcium channel from neurons in mammals and cephalopods utilizing a toxin fraction (FTX) from funnel-web spider poison, Proc. Natl. Acad. Sci. U.S.A., Mar. 1989, vol. 86, No. 5, pp. 1689-1693.

European CGRP in Subarachnoid Haemorrhage Study Group, "Effect of calcitonin-gene-related peptide in patients with delayed postoperative cerebral ischaemia after aneurysmal subarachnoid haemorrhage," Lancet, (1992), vol. 339, pp. 831-834.

Dorhout Mees, S. et al., "Calcium antagonists for aneurysmal subarachnoid haemorrhage," Cochrane Database of Systemic Reviews, (2007), Issue 3, pp. 1-50.

Haley, E.C. Jr. et al., "A randomized trial of two doses of nicardipine in aneurysmal subarachnoid hemorrhage," J. Neurosurg., (1994), vol. 80, pp. 788-796.

Jang, Y.G., et al., "Metaanalysis of Tirilazad Mesylate in Patients with Aneurysmal Subarachnoid Hemorrhage," Neurocrit Care, (2009), vol. 10, 141-147.

Nieuwkamp, D.J. et al., "Changes in case fatality of aneurysmal subarachnoid haemorrhage over time, according to age, sex, and region: a meta-analysis," Lancet Neurol, (2009), vol. 8, pp. 635-642.

Van Gijn, J. and Rinkel G.J.E., "Subarachnoid haemorrhage: diagnosis, causes and management," Brain, (2001), vol. 124, pp. 249-278.

Vergouwen, M.D.I. et al., "Effect of Statin Treatment on Vasospasm, Delayed Cerebral Ischemia, and Functional Outcome in Patients With Aneurysmal Subarachnoid Hemorrhage: A Systemic Review and Meta-Analysis Update," Stroke, (2010), vol. 41, pp. e47-e52.

Wong, G.K.C. et al., "Intravenous Magnesium Sulfate for Aneurysmal Subarachnoid Hemorrhage (IMASH): A Randomized, Double-Blinded, Placebo-Controlled, Multicenter Phase III Trial," Stroke, (2010), vol. 41, pp. 921-926.

Mayberg Marc R. et al., "The role of hemoglobin in arterial narrowing after subarachnoid hemorrhage," J. Neurosurg. (1990), vol. 72, pp. 634-640.

* cited by examiner

DRUG DELIVERY SYSTEM FOR THE PREVENTION OF CEREBRAL VASOSPASM

CROSS REFERENCE

This application claims priority under Title 35, United States Code 119(e) from Provisional Application Ser. No. 60/943,124, filed Jun. 11, 2007, and Provisional Application Ser. No. 60/976,902, filed Oct. 2, 2007.

FIELD OF INVENTION

The invention relates to a delivery system of compounds targeting at least one cerebral artery to prevent and/or reduce the occurrence of or severity of cerebral vasospasm, and or constriction of at least one cerebral artery due to other conditions, such as head injury, atherosclerosis, or stenosis after angioplasty and stenting.

BACKGROUND

The human brain constitutes only about 2% of the total weight of the body, but it receives about 15% of the cardiac output, and its oxygen consumption is approximately 20% of that for the total body. These values indicate the high metabolic rate and oxygen requirement of the brain. These needs are met by a correspondingly high rate of blood flow per unit brain weight. Cerebral circulation is supplied by the internal cartoid arteries and the vertebral arteries. The total blood flow to the brain is about 750-1000 ml/min; of this amount about 350 ml flows through each internal carotid and about 100-200 ml flows through the vertebral basilar system. The venous outflow is drained by the internal jugular veins and the vertebral veins.

The term "stroke" or "cerebrovascular accident" as used herein refers to the neurological symptoms and signs, usually focal and acute, that result from diseases involving blood vessels. Strokes are either occlusive (due to closure of a blood vessel) or hemorrhagic (due to bleeding from a vessel). The term "ischemia" as used herein refers to insufficiency of blood supply. When ischemia is sufficiently severe and prolonged, neurons and other cellular elements die; this condition is referred to as "infarction."

Hemorrhage may occur at the brain surface (extraparenchymal), for example from the rupture of congenital aneurysms at the circle of Willis, causing subarachnoid hemorrhage (SAH). Hemorrhage also may be intraparenchymal, for example from rupture of vessels damaged by long-standing hypertension, and may cause a blood clot (intracerebral hematoma) within the cerebral hemispheres, in the brain stem, or in the cerebellum. Hemorrhage may be accompanied by ischemia or infarction. The mass effect of an intracerebral hematoma may compromise the blood supply of adjacent brain tissue; or subarachnoid hemorrhage may cause reactive vasospasm of cerebral surface vessels, leading to further ischemic brain damage. Infarcted tissue may also become secondarily hemorrhagic. Aneurysms occasionally can rupture into the brain causing an intracerebral hematoma and into the cerebral ventricles causing intraventricular hemorrhage.

Although most occlusive strokes are due to atherosclerosis and thrombosis and most hemorrhagic strokes are associated with hypertension or aneurysms, strokes of either type may occur at any age from many causes, including: cardiac disease, trauma, infection, neoplasm, blood dyscrasia, vascular malformation, immunological disorder, and exogenous toxins.

Cerebral Arteries

FIG. 1 is a schematic illustration of the brain's blood vessels. Each cerebral hemisphere is supplied by an internal carotid artery, which arises from a common carotid artery beneath the angle of the jaw, enters the cranium through the carotid foramen, traverses the vacernosus sinus (giving off the ophthalmic artery), penetrates the dura and divides into the anterior and middle cerebral arteries. The large surface branches of the anterior cerebral artery supply the cortex and white matter of the inferior frontal lobe, the medial surface of the frontal and parietal lobes and the anterior corpus callosum. Smaller penetrating branches supply the deeper cerebrum and diencephalon, including limbic structures, the head of the caudate, and the anterior limb of the internal capsule. The large surface branches of the middle cerebral artery supply most of the cortex and white matter of the hemisphere's convexity, including the frontal, parietal, temporal and occipital lobes, and the insula. Smaller penetrating branches supply the deep white matter and diencephalic structures such as the posterior limb of the internal capsule, the putamen, the outer globus pallidus, and the body of the caudate. After the internal carotid artery emerges from the cavernous sinus, it also gives off the anterior choiroidal artery, which supplies the anterior hippocampus and, at a caudal level, the posterior limb of the internal capsule. Each vertebral artery arises from a subclavian artery, enters the cranium through the foramen magnum, and gives off an anterior spinal artery and a posterior inferior cerebellar artery. The vertebral arteries join at the junction of the pons and the medulla to form the basilar artery, which at the level of the pons gives off the anterior inferior cerebellar artery and the internal auditory artery, and, at the midbrain, the superior cerebellar artery. The basilar artery then divides into the two posterior cerebral arteries. The large surface branches of the posterior cerebral arteries supply the inferior temporal and medial occipital lobes and the posterior corpus callosum; the smaller penetrating branches of these arteries supply diencephalic structures, including the thalamus and the subthalamic nuclei, as well as part of the midbrain (see Principles of Neural Sciences, 2d Ed., Eric R. Kandel and James H. Schwartz, Elsevier Science Publishing Co., Inc., New York, 1985, pp. 854-56).

Interconnections between blood vessels (anastomoses) protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branches of the middle, anterior, and posterior cerebral arteries (Principles of Neural Sciences, 2d Ed., Eric R. Kandel and James H. Schwartz, Elsevier Science Publishing Co., Inc., New York, 1985, pp. 854-56).

The terms "anastomosis" and "anastomoses" as used herein refer interchangeably to interconnections between blood vessels. These interconnections protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branchs of the middle, anterior, and posterior cerebral arteries (Principles of Neural Sciences, 2d Ed., Eric R. Kandel and James H. Schwartz, Elsevier Science Publishing Co., Inc., New York, 1985, pp. 854-56).

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

Vasoconstriction and Vasodilation

The term "vasoconstriction" as used herein refers to the narrowing of the blood vessels resulting from contracting of the muscular wall of the vessels. When blood vessels constrict, the flow of blood is restricted or slowed. The term "vasodilation" which is the opposite of vasoconstriction as used herein refers to the widening of blood vessels. The terms "vasoconstrictors," "vasopressors," or "pressors" as used herein refer to factors causing vasoconstriction. Vasoconstriction usually results in an increase of the blood pressure and may be slight or severe. Vasoconstriction may result from disease, medication, or psychological conditions. Medications that cause vasoconstriction include, but are not limited to, antihistamines, decongestants, methylphenidate, cough and cold combinations, pseudoephedrine, and caffeine.

A vasodilator is a drug or chemical that relaxes the smooth muscle in blood vessels causing them to dilate. Dilation of arterial blood vessels (mainly arterioles) leads to a decrease in blood pressure. The relaxation of the smooth muscle relies on removing the stimulus for contraction, which depends predominately on intracellular calcium ion concentrations and phosphorylation of myosin light chain (MLC). Thus, vasodilation predominantly works by either 1) lowering intracellular calcium concentration, or 2) dephosphorylation of MLC which includes the stimulation of myosin light chain phosphatase and the induction of calcium symporters and antiporters (which pump calcium ions out of the intracellular compartment). The re-uptake of ions into the sarcoplasmic reticulum of smooth muscle via exchangers and expulsion across the plasma membrane also helps to accomplish vasodilation. The specific mechanisms to accomplish these effects varies from vasodilator to vasodilator and may be grouped as endogenous and exogenous. The term "endogenous" as used herein refers to proceeding from within or derived internally; resulting from conditions within the organism rather than externally caused. The term "exogenous" as used herein refers to originating from outside; derived externally; externally caused rather than resulting from conditions within the organism.

Vasodilation directly affects the relationship between mean arterial pressure and cardiac output and total peripheral resistance (TPR). Cardiac output may be computed by multiplying the heart rate (in beats/minute) and the stroke volume (the volume of blood ejected during systole). TPR depends on several factors, including, but not limited to, the length of the vessel, the viscosity of blood (determined by hematocrit), and the diameter of the blood vessel. The latter is the most important variable in determining resistance. An increase in either cardiac output or TPR cause a rise in the mean arterial pressure. Vasodilators work to decrease TPR and blood pressure through relaxation of smooth muscle cells in the tunica media layer of large arteries and smaller arterioles.

Vasodilation occurs in superficial blood vessels of warm-blooded animals when their ambient environment is hot; this process diverts the flow of heated blood to the skin of the animal, where heat may be more easily released into the atmosphere. The opposite physiological process is vasoconstriction. Vasodilation and vasoconstriction are modulated naturally by local paracrine agents from endothelial cells (e.g, bradykinin, adenosine), as well as by an organism's autonomic nervous system and adrenal glands, both of which secrete catecholamines, such as norepinephrine and epinephrine, respectively.

Vasodilators are used to treat conditions such as hypertension, where the patient has an abnormally high blood pressure, as well as angina and congestive heart failure, where maintaining a lower blood pressure reduces the patient's risk of developing other cardiac problems.

Subarachnoid Hemorrhage

The brain is encased by three layers of membranes or meninges: the pia mater, arachnoid mater, and dura mater. The subarachnoid space is the area between the arachnoid membrane and the pia mater surrounding the brain. The term "subarachnoid hemorrhage" (also referred to as "SAH") refers to bleeding into the subarachnoid space. SAH may occur spontaneously, usually from a cerebral aneurysm, or may result from trauma. Symptoms include an intense headache with a rapid onset (sometimes referred to as a "thunderclap headache"), vomiting, and an altered level of consciousness. Diagnosis generally is made with computed tomography (CT scanning), or occasionally by lumbar puncture. Treatment is by close observation, medication and early neurosurgical investigations and treatments to prevent recurrence and complications.

SAH is a medical emergency and may lead to death or severe disability—even if recognized and treated at an early stage. Half of all SAH cases are fatal, with 10-15% dying before arriving at a hospital. SAH is considered a form of stroke, and causes between 1 and 7% of all strokes. Where caused by a rupture of an intracranial aneurysm, bleeding is seen in the subarachnoid space and less commonly in the intravascular and intracerebral spaces most frequently. Bleeding due to SAH may result in brain damage, brain shift, decreased cerebral perfusion and hydrocephalus. It is estimated that the incidence of SAH from a ruptured intracranial aneurysm in the U.S. is 1 case per 10,000 persons, yielding approximately 27,000-30,000 new cases of SAH each year. These ruptured aneurysms have a 30-day mortality rate of 45%. Further, an estimated 30% of survivors will have moderate-to-severe disability.

Patients who survive SAH also are at risk of secondary complications. Among the complications are, most notably, aneurysmal re-bleeding and cerebral vasospasm. Cerebral vasospasm is a consequence of SAH, but also can occur after any condition that deposits blood in the subarachnoid space. More specifically, the term "cerebral vasospasm" refers to the narrowing of the large capacitance arteries at the base of the brain (i.e., cerebral arteries) following hemorrhage into the subarachnoid space, and leads to reduced perfusion of distal brain regions.

Symptoms

The classic symptom of SAH is thunderclap headache (a headache described as the "worst ever" or a "kick in the head," developing over seconds to minutes) although it is a symptom in only about a third of all SAH patients. Approximately 10% of patients who seek medical care with this symptom have an underlying SAH. Patients also may present with vomiting, and 1 in 14 have seizures. Neck stiffness and other signs of meningism may be present, as may confusion, decreased level of consciousness, or coma. Intraocular hemorrhage may occur in response to the raised pressure around the brain. Subhyaloid (the hyaloid membrane envelopes the vitreous body of the eye) and vitreous hemorrhage may be visible on fundoscopy. This is known as Terson syndrome (occurring in 3-13% of cases), and is more common in more severe SAH. In a patient with thunderclap headache, none of the signs mentioned are helpful in confirming or ruling out hemorrhage, although seizures are more common if the bleeding is the result of a ruptured aneurysm as opposed to other causes. Oculomotor nerve abnormalities (affected eye looking downward and outward, inability to lift the eyelid on the same side but normal pupillary reflexes) may indicate bleeding from an aneurysm arising near the posterior communicating artery. Isolated dilation of a pupil may also reflect brain herniation as a result of rising intracranial pressure. The body releases large amounts of adrenaline and similar hormones as a result of the bleeding, which leads to a sharp increase in the blood pressure. The heart comes under substantial strain, and neurogenic pulmonary edema, cardiac arrhythmias, electrocardiographic changes (with occasional giant inverted "cerebral" T waves) and cardiac arrest (3%) may rapidly occur after the onset of hemorrhage.

SAH also may occur in people who have suffered a head injury. Symptoms may include headache, decreased level of consciousness or hemiparesis. It is regarded as a severe complication of head injury, especially if it is associated with lower Glasgow Coma Scale levels.

Diagnosis

The initial steps for evaluating a person with a suspected SAH are the steps of obtaining a medical history and performing a physical examination. Since only 10-25% of patients admitted to a hospital with a thunderclap headache are suffering from a SAH, other possible causes usually are considered simultaneously, such as meningitis, migraine, and cerebral venous sinus thrombosis. Intracerebral hemorrhage, which is twice as common as SAH, occasionally is misdiagnosed as SAH.

A diagnosis of SAH cannot be made on clinical grounds alone. Generally, medical imaging [usually computed tomography (CT scan) which has a high sensitivity (>95% correct identification especially on the first day after the onset of bleeding)] of the brain is required to confirm or exclude bleeding. Magnetic resonance imaging (MRI scan) may be more sensitive after several days when compared to CT. In people with normal CT or MRI scans, lumbar puncture, in which cerebrospinal fluid (CSF) is removed with a needle from the lumbar sac, shows evidence of hemorrhage in 3% of the group in whom the CT was found to be normal; lumbar puncture is therefore regarded as mandatory if imaging is negative. The CSF sample is examined for xanthochromia, the yellow appearance of centrifugated fluid, or using spectrophotometry for bilirubin, a breakdown product of hemoglobin in the CSF.

After a SAH is confirmed, its origin needs to be determined. CT angiography (visualizing blood vessels with radiocontrast on a CT scan) to identify aneurysms is generally the first step, although the more invasive catheter angiography (injecting radiocontrast through a catheter advanced to the brain arteries) is the gold standard test but has a higher risk of complications. The latter is useful if there are plans to obliterate the source of bleeding, such as an aneurysm, at the same time.

Causes

Spontaneous SAH most often is due to rupture of cerebral aneurysms (85%). Cerebral aneurysms are weaknesses in the walls of arteries of the brain that become enlarged. They tend to be located in the circle of Willis and its branches. While most cases of SAH are due to bleeding from small aneurysms, larger aneurysms (which are rarer) are more likely to rupture. No aneurysm is detected from the first angiogram in 15-20% of cases of spontaneous SAH. Non-aneurysmal perimesencephalic hemorrhage, in which the blood is limited to the area of the midbrain, causes another 10% of SAH cases. In these, no aneurysms are generally found. The remaining 5% of cases are due to vasculitic damage to arteries, other disorders affecting the vessels, disorders of the spinal cord blood vessels, and bleeding into various tumors. Most traumatic SAHs occur near a skull fracture or intracerebral contusion.

Classification

Several grading scales are available for SAH. These have been derived by retrospectively matching characteristics of patients with their outcomes. In addition to the ubiquitously used Glasgow Coma Scale (GCS), three other specialized scores are in use. In all scores, a higher number is associated with a worse outcome. The first scale of severity was described by Hunt and Hess in 1968 ("Hunt and Hess scale") and categorizes the clinical condition of the patient. The Fisher Grade classifies the appearance of SAH on CT scan. The Fisher scale has been modified by Claassen and coworkers ("Claassen scale"), reflecting the additive risk from SAH size and accompanying intraventricular hemorrhage. The World Federation of Neurosurgeons classification uses GCS and focal neurological deficit to gauge severity of symptoms. A comprehensive classification scheme has been suggested by Ogilvy and Carter to predict outcome and gauge therapy. The Ogilvy system has five grades, assigning one point for the presence or absence of each of five factors: age greater than 50; Hunt and Hess grade 4 or 5; Fischer scale 3 or 4; aneurysm size greater than 10 mm; and posterior circulation aneurysm 25 mm or more.

Treatment

The management of SAH consists of general measures to stabilize the patient, specific measures to prevent rebleeding by obliterating the bleeding source, prevention of vasospasm, and prevention and treatment of complications.

General Measures

The first priority is to stabilize the patient. Those with a depressed level of consciousness may need to be intubated and mechanically ventilated. Blood pressure, pulse, respiratory rate and Glasgow Coma Scale are monitored frequently. Once the diagnosis is confirmed, admission to an intensive care unit may be preferable, especially given that 15% have a further episode (rebleeding) in the first hours after admission. Nutrition is an early priority, with oral or nasogastric tube feeding being preferable over parenteral routes. Analgesia (pain control) generally is restricted to non-sedating agents such as codeine, as sedation may impact on the mental status and thus interfere with the ability to monitor the level of consciousness. Deep vein thrombosis is prevented with compression stockings, intermittent pneumatic compression of the calves, or both.

Prevention of rebleeding

Patients with a large hematoma associated with depressed level of consciousness or focal neurological symptoms may be candidates for urgent surgical removal of the blood and occlusion of the bleeding aneurysm. A catheter or tube may be inserted into the ventricles to treat hydrocephalus. The remainder are stabilized more extensively, and undergo a transfemoral catheter angiogram or CT angiogram later. After the first 24 hours, rebleeding risk remains about 40% over the subsequent four weeks, suggesting that interventions should be aimed at reducing this risk.

If a cerebral aneurysm is identified on angiography, two measures are available to reduce the risk of further bleeding from the same aneurysm: clipping and coiling. Clipping requires a craniotomy (opening of the skull) to locate the aneurysm, followed by the placement of a clip or clips across the neck of the aneurysm. Coiling is performed through the large blood vessels: a catheter is inserted into the femoral artery in the groin, and advanced through the aorta to the arteries (both carotid arteries and both vertebral arteries) that supply the brain. When the aneurysm has been located, platinum coils are deployed that lead to formation of a blood clot in the aneurysm and obliteration. The decision as to which treatment is undertaken typically is made by a multidisciplinary team, including a neurosurgeon and a neuroradiologist. Rebleeding is hard to predict but may happen at any time and carries a dismal prognosis. Interventions to prevent rebleeding, principally clipping or coiling the ruptured aneurysm, therefore are performed as early as possible.

Aneurysms of the middle cerebral artery and its related vessels are hard to reach with angiography and tend to be amenable to clipping, while those of the basilar artery and posterior cerebral artery are hard to reach surgically and are more accessible for endovascular management. The main drawback of coiling is the possibility that the aneurysm will recur; this risk is extremely small in the surgical approach. Patients who have undergone coiling are typically followed up for many years with angiography or other measures to ensure recurrence of aneurysms is identified early.

Prognosis

Early Morbidity and Mortality

The mortality rate for SAH is between 40% and 50%. Of those who survive initial hospitalization, treatment and complications, more than 25% have significant restrictions in their lifestyle, and less than 20% have no residual symptoms whatsoever. Delay in diagnosis of minor SAH without coma (or mistaking the sudden headache for migraine) contributes to poor outcome. Risk factors for poor outcome include higher age, poorer neurological grade, more blood and larger aneurysm on the initial CT scan, location of an aneurysm in the posterior circulation, systolic hypertension, and a previous diagnosis of heart attack, hypertension, liver disease or a previous SAH. During the hospital stay, occurrence of delayed ischemia resulting from vasospasm, development of intracerebral hematoma or intraventricular hemorrhage (bleeding into the ventricles of the brain), and presence of fever on the eighth day of admission also worsen the prognosis.

SAH that does not show an aneurysm by complete catheter angiography may be referred to as "angiogram-negative SAH." This carries a better prognosis than SAH from an aneurysm; however, it still is associated with a risk of ischemia, rebleeding and hydrocephalus. Perimesencephalic SAH (bleeding around the mesencephalon part of the brain), however, has a very low rate of rebleeding or delayed ischemia, and the prognosis of this subtype is excellent.

Long-Term Outcomes

Neurocognitive symptoms, such as fatigue, mood disturbances, and other related symptoms, are common in people who have suffered SAH. Even in those who have made a good neurological recovery, anxiety, depression, posttraumatic stress disorder and cognitive impairment are common. Over 60% report frequent headaches. Aneurysmal SAH may lead to damage of the hypothalamus and the pituitary gland, two areas of the brain that play a central role in hormonal regulation and production. Studies indicate that more than 25% of people with a previous SAH may develop deficiencies in one or more of the hypothalamic-pituitary hormones such as growth hormone, prolactin or thyroid-stimulating hormone.

Some studies indicate the incidence of SAH is on average 9.1 per 100,000 annually. Studies from Japan and Finland show higher rates in those countries (22.7 per 100,000 and 19.7 per 100,000, respectively), for reasons that are not entirely understood. South and Central America, in contrast, have a rate of 4.2 per 100,000 on average. The group of people at risk for SAH is younger than the population usually affected by stroke, but the risk still increases with age. Young people are much less likely than middle-aged people (risk ratio 0.1, or 10%) to suffer a SAH. The risk continues to rise with age and is 60% higher in the very elderly (over 85) than in those between 45 and 55. Risk of SAH is about 25% higher in women above 55, potentially reflecting the hormonal changes that result from the menopause.

Vasospasm

Vasospasm is the most common cause of focal ischemia after SAH. It adversely affects outcome in patients with SAH as it accounts for up to 23% of SAH-related disability and death. Of all types of ischemic stroke, vasospasm is unique in that it is to some degree predictable, preventable, and treatable (see Macdonald, R. L. and Weir, B. In Cerebral Vasospasm. 2001. Academic Press, Burlington, Mass., USA).

Each year, about 1 in 10,000 people have an aneurysm rupture. Mortality and morbidity increase with the volume of hemorrhage and reflect the age and health status of the patient, with the chance of developing an aneurysm increasing steadily with age. Rebleeding is exceptionally adverse due to the increase in volume of SAH as well as the increased likelihood of extension into the brain and ventricles. Most deaths resulting from aneurysmal rupture occur outside of hospitals or shortly after admission due to the effects of the initial bleed or early rebleeding. Potential manifestation of symptoms from vasospasm occurs only in those patients who survive past the first few days.

The incidence of vasospasm is less than the incidence of SAH (since only some patients with SAH develop vasospasm). The incidence of vasospasm will depend on the type of patient a given hospital receives and the methods by which vasospasm is diagnosed. The unqualified term "vasospasm" is usually used with reference to angiographically determined arterial narrowing. Clinical vasospasm most often is used synonymously with delayed cerebral ischemia (DCI). When used in another fashion, for instance, vasospasm based on increased middle cerebral artery transcranial Doppler velocities, this should be specified.

Some degree of angiographic narrowing will occur in at least two-thirds of patients having angiography between 4 and 12 days after SAH. The numbers of patients developing neurological deterioration from this DCI varies with the diligence with which the patient is monitored and the efficacy of prophylaxis, but it has been estimated at about one-third. Of hospitalized SAH patients, between 5 to 10% die from vasospasm. When compared to post-SAH patients of intermediate grade, post-SAH patients in very good condition are less likely to develop vasospasm as they have small volume SAH, while post-SAH patients in very poor condition are more likely to die earlier from the initial episode. The presence of thick, widespread subarachnoid clot which can be visualized on the computerized tomographic (CT) scan done in close proximity to the bleeding episode is a key prognostic factor. The absence of blood on the initial CT scan is indicative that vasospasm is very unlikely in the absence of rebleeding. The chance of vasospasm and consequently DCI is decreased by factors decreasing the duration of exposure to clot. Conversely, the incidence of vasospasm and DCI is increased by the utilization of antifibrinolytic drugs which prolong the exposure of arteries to clot and possibly cause ischemia by other mechanisms. Poor admission clinical grade is associated with DCI, presumably because they both indicate larger volumes of SAH. A definite relationship between age, hypertension, or sex and DCI has not been established. It is likely that smokers are more prone to vasospasm and DCI. Factors unrelated to the development of vasospasm include season, geography, contrast material, and diabetes.

Patients who develop vasospasm do worse than those who do not. If surgery or aneurysm coiling is performed earlier (within the first day or so) the outcome tends to be better than if treatment is delayed. When operations were preferentially performed during the peak period for vasospasm outcomes were generally worse. Vasospasm does not result from early surgery or coiling; early surgery or coiling permits more vigorous treatment should vasospasm develop. If a thick clot is present, an attempt at careful removal should be made. The amount of residual clot postoperatively is a prognostic factor for DCI. Open operation exposes the patient to retractor pressure, venous sacrifice, temporary clipping ischemia, brain removal, and arterial injury. Studies have shown post operative decrease in cerebral blood flow, regional cerebral metabolic rate of oxygen, and oxygen extraction ratio.

Independent variables, such as admission neurologic grade, increasing age, and massive intracranial or intraventricular hemorrhage, are more closely linked to outcome than vasospasm. Since vasospasm is a graded process it is expected that only the extreme cases will result in infarction in the absence of systemic hypotension, cardiac dysfunction, anoxia, and intracranial hypertension. Preexisting hypertension and advanced age also strongly influence the vulnerability of the brain to ischemia. The etiological relationship between vasospasm and infarction in fatal cases is not in dispute.

There is evidence that vasospasm may be reduced by clot removal either surgically or pharmacologically. There also are data suggesting that DCI may be lessened by hypertension and hypervolemia as well as by calcium antagonists. Vasospasm also may be abolished by mechanical or pharmacologic angioplasty.

Incidence of Vasospasm

The incidence of angiographic vasospasm depends on the interval after the SAH. The peak incidence occurs 6-8 days after SAH (range, 3-12 days). In addition to the time after the SAH, the other principal factors that affects the prevalence of vasospasm are the volume and distribution of subarachnoid blood.

Prognostic Factors for Vasospasm

Prognostic factors for vasospasm include: blood on CT scan; hypertension; anatomical and systemic factors; clinical grade; antifibrinolytics; age and sex; smoking; physiological parameters; and hydrocephalus.

Diagnosis

The diagnosis of vasospasm is primarily clinical. Vasospasm can be asymptomatic; however, when the cerebral blood flow is below ischemic threshold, symptoms become apparent. Symptoms typically develop subacutely and may fluctuate. Symptoms may include excess sleepiness, lethargy, stupor, hemiparesis or hemiplegia, abulia, language disturbances, visual fields deficits, gaze impairment, and cranial nerve palsies. Although some symptoms are localized, they are not diagnostic of any specific pathological process; therefore alternative diagnoses, such as rebleeding, hydrocephalus, and seizures, should be promptly excluded using radiographic, clinical and laboratory assessments. Cerebral angiography is the gold standard for visualizing and studying cerebral arteries; transcranial Doppler ultrasonography is also utilized.

The pathophysiology of vasospasm may involve structural changes and biochemical alterations within the vascular endothelium and smooth muscle cells. The presence of blood in the subarachnoid space may initiate these changes. In addition, hypovolemia and an impaired cerebral autoregulatory function may concurrently interfere with cerebral perfusion. The cumulative effects of these processes can lead to reduction in cerebral blood flow so severe as to cause cerebral ischemia leading to infarction. Additionally, a period of severe constriction could lead to morphologic changes in the walls of the cerebral arteries, which may cause them to remain narrowed without the continued presence of vasoactive substances. The area of the brain supplied by the affected artery then would experience ischemia (meaning a restriction in blood supply).

Other Complications

Hydrocephalus (obstruction of the flow of cerebrospinal fluid) may complicate SAH in both the short-and long-term, and may be detected on CT scanning. If the level of consciousness is decreased, surgical drainage of the excess fluid (for instance with a ventricular drain or shunt) is occasionally necessary.

Fluctuations in blood pressure and electrolyte disturbances, as well as pneumonia and cardiac decompensation, occur in about 50% of hospitalized patients with SAH, and may worsen prognosis. They are managed symptomatically.

Seizures occur in about a third of all cases.

Treatments

Nimodipine, an oral calcium channel blocker, has been shown in clinical trials to reduce the chance of a poor outcome, however it may not significantly reduce the amount of vasospasm detected on angiography. Other calcium channel blockers and magnesium sulfate have been studied, but are not presently recommended. There is no evidence that shows benefit if nimodipine is given intravenously. In traumatic SAH, nimodipine does not affect long-term outcome, and is not recommended.

Hemodynamic manipulations, previously referred to as "triple H" therapy, often is used as a measure to treat vasospasm. This entails the use of intravenous fluids to achieve a state of hypertension (high blood pressure), hypervolemia (excess fluid in the circulation) and hemodilution (mild dilution of the blood). Induced hypertension is believed to be the most important component of this treatment although evidence for the use of this approach is inconclusive, and no sufficiently large randomized controlled trials ever have been undertaken to demonstrate its benefits.

If symptomatic vasospasm is resistant to medical treatment, angiography may be attempted to identify the sites of vasospasm and to administer vasodilator medication (drugs that relax the blood vessel wall) directly into the artery (pharmacological angioplasty), and mechanical angioplasty (opening the constricted area with a balloon) may be performed.

Voltage-Gated Ion Channels

Voltage-gated ion channels are a class of transmembrane ion channels that are activated by changes in electrical potential difference near the channel; these types of ion channels are especially critical in neurons, but are common in many types of cells. They have an important role in excitable neuronal and muscle tissues as they allow a rapid and coordinated depolarization in response to triggering voltage change. Positioned along the axon and at the synapse, voltage-gated ion channels directionally propagate electrical signals.

Structure

Voltage-gated ion channels generally are composed of several subunits arranged such that there is a central pore through which ions can travel down their electrochemical gradients. The channels tend to be quite ion-specific, although similarly sized and charged ions may also travel through them to some extent.

Mechanism

Crystallographic structural studies of a potassium channel, assuming that this structure remains intact in the corresponding plasma membrane, suggest that when a potential difference is introduced over the membrane, the associated electromagnetic field induces a conformational change in the potassium channel. The conformational change distorts the shape of the channel proteins sufficiently such that the channel, or cavity, opens to admit ion influx or efflux to occur across the membrane, down its electrochemical gradient. This subsequently generates an electrical current sufficient to depolarize the cell membrane.

Voltage-gated sodium channels and calcium channels are made up of a single polypeptide with four homologous domains. Each domain contains 6 membrane spanning alpha helices. The voltage sensing helix, S4, has multiple positive charges such that a high positive charge outside the cell repels the helix and induces a conformational change such that ions may flow through the channel. Potassium channels function in a similar way, with the exception that they are composed of four separate polypeptide chains, each comprising one domain. The voltage-sensitive protein domain of these channels (the "voltage sensor") generally contains a region composed of S3b and S4 helices, known as the "paddle" due to its shape, which appears to be a conserved sequence.

Voltage-Dependant Calcium Channels

Voltage-dependent calcium channels (VDCC) are a group of voltage-gated ion channels found in excitable cells (e.g., muscle, glial cells, neurons, etc.) with a permeability to calcium ions ($Ca^{2+}$). At physiologic or resting membrane potential, VDCCs are normally closed. They are activated (i.e., opened) at depolarized membrane potentials. Activation of particular VDCCs allows $Ca^{2+}$ entry into the cell; muscular contraction, excitation of neurons, up-regulation of gene expression, or release of hormones or neurotransmitters results depending upon the cell type.

Voltage-dependent calcium channels are formed as a complex of several different subunits: $\alpha 1$, $\alpha 2\delta$, $\beta 1$-$4$, and $\gamma$. The $\alpha 1$ subunit forms the ion conducting pore while the associated subunits have several functions including modulation of gating.

$\alpha 1$ Subunit

The $\alpha 1$ subunit pore (~190 kDa in molecular mass) is the primary subunit necessary for channel functioning in the VDCC, and consists of the characteristic four homologous I-IV domains containing six transmembrane $\alpha$-helices each. The $\alpha 1$ subunit forms the $Ca^{2+}$ selective pore, which contains voltage-sensing machinery and the drug/toxin-binding sites. Ten $\alpha 1$ subunits that have been identified in humans.

$\alpha 1\delta$ Subunit

The $\alpha 2\delta$ gene encodes two subunits, $\alpha 2$ and $\delta$. They are linked to each other via a disulfide bond and have a combined molecular weight of 170 kDa. The $\alpha 2$ is the extracellular glycosylated subunit that interacts the most with the $\alpha 1$ subunit. The $\delta$ subunit has a single transmembrane region with a short intracellular portion, which serves to anchor the protein in the plasma membrane. There are 4 $\alpha 2\delta$ genes: CACNA2D1 (CACNA2D1), (CACNA2D2), (CACNA2D3), and (CACNA2D4). Co-expression of the $\alpha 2\delta$ enhances the level of expression of the $\alpha 1$ subunit and causes an increase in current amplitude, faster activation and inactivation kinetics and a hyperpolarizing shift in the voltage dependence of inactivation. Some of these effects are observed in the absence of the beta subunit, whereas, in other cases, the co-expression of beta is required. The $\alpha 2\delta$-1 and $\alpha 2\delta$-2 subunits are binding sites for at least two anticonvulsant drugs, gabapentin and pregabalin, that also find use in treating chronic neuropathic pain.

$\beta$ Subunit

The intracellular $\beta$ subunit (55 kDa) is an intracellular membrane-associated guanylate kinase (MAGUK)-like protein containing a guanylate kinase (GK) domain and an SH3 (src homology 3) domain. The guanylate kinase domain of the $\beta$ subunit binds to the $\alpha 1$ subunit I-II cytoplasmic loop and regulates HVGCC activity. There are four known isoforms of the $\beta$ subunit: CACNB1, CACNB2, CACNB3, and CACNB4.

Without being limited by theory, it is postulated the cytosolic $\beta$ subunit has a major role in stabilizing the final $\alpha 1$ subunit conformation and delivering it to the cell membrane by its ability to mask an endoplasmic reticulum retention signal in the α1 subunit. The endoplasmic retention brake is contained in the I-II loop in the α1 subunit that becomes masked when the β subunit binds. Therefore the β subunit functions initially to regulate the current density by controlling the amount of α1 subunit expressed at the cell membrane.

In addition to this potential trafficking role, the β subunit has the added important functions of regulating activation and inactivation kinetics, and hyperpolarizing the voltage-dependence for activation of the α1 subunit pore, so that more current passes for smaller depolarizations. The β subunit acts as an important modulator of channel electrophysiological properties. The interaction between a highly conserved 18-amino acid region on the α1 subunit intracellular linker between domains I and II (the Alpha Interaction Domain, AIDBP) and a region on the GK domain of the β subunit (Alpha Interaction Domain Binding Pocket) is responsible for the regulatory effects exerted by the β subunit. Additionally, the SH3 domain of the β subunit also gives added regulatory effects on channel function, indicating that the β subunit may have multiple regulatory interactions with the α1 subunit pore. The AID sequence does not appear to contain an endoplasmic reticulum retention signal; this may be located in other regions of the I-II α1 subunit linker.

γ Subunit

The γ1 subunit is known to be associated with skeletal muscle VGCC complexes, but the evidence is inconclusive regarding other subtypes of calcium channel. The γ1 subunit glycoprotein (33 kDa) is composed of four transmembrane spanning helices. The γ1 subunit does not affect trafficking, and, for the most part, is not required to regulate the channel complex. However, γ2, γ3, γ4 and γ8 also are associated with AMPA glutamate receptors. There are 8 genes for gamma subunits: γ1 (CACNG1), γ2 (CACNG2), γ3 (CACNG3), γ4 (CACNG4), (CACNG5), (CACNG6), (CACNG7), and (CACNG8).

Voltage dependent calcium channels vary greatly in structure and form. Calcium channels are classified as L-, N-, P/Q, T- and R-type according to their pharmacological and electrophysiological properties. These channel subtypes have distinct physiological functions. Molecular cloning has clarified the α1 subunit sequence of each channel. The α1 subunit has a specific role in eliciting activity in an individual channel. Nonetheless, selective blockers for these channel subtypes are required for defining specific channels involved in each activity. The neural N-type channels are blocked by ω-conotoxin GVIA; the R-type channels are resistant to other blockers and toxins, are blocked by SNX-482, and may be involved in processes in the brain; the closely related P/Q-type channels are blocked by ω-agatoxins. The dihydropyridine-sensitive L-type channels are responsible for excitation-contraction coupling of skeletal, smooth, and cardiac muscle and for hormone secretion in endocrine cells and also are antagonized by phenylalkylamines and benzothiazepines.

Types of Voltage-Gated Calcium Channels

L-Type Calcium Channels

L-type voltage-gated calcium channels are opened when a smooth muscle cell is depolarized. This depolarization may be brought about by stretching of the cell, by agonist-binding its G protein-coupled receptor (GPCR), or by autonomic nervous system stimulation. Opening of the L-type calcium channel causes influx of extracellular $Ca^{2+}$, which then binds calmodulin. The activated calmodulin molecule activates myosin light-chain kinase (MLCK), which phosphorylates the myosin in thick filaments. Phosphorylated myosin is able to form crossbridges with actin thin filaments, and the smooth muscle fiber (i.e., cell) contracts via the sliding filament mechanism.

L-type calcium channels also are enriched in the t-tubules of striated muscle cells, such as, skeletal and cardiac myofibers. As in smooth muscle, L-type calcium channels open when these cells are depolarized. In skeletal muscle, since the L-type calcium channel and the calcium-release channel (ryanodine receptor, or RYR) are mechanically gated to each other with the latter located in the sarcoplasmic reticulum (SR), the opening of the L-type calcium channel causes the opening of the RYR. In cardiac muscle, opening of the L-type calcium channel permits influx of calcium into the cell. The calcium binds to the calcium release channels (RYRs) in the SR, opening them (referred to as "calcium-induced calcium release" or "CICR"). $Ca^{2+}$ is released from the SR and is able to bind to troponin C on the actin filaments regardless of how the RYRs are opened, either through mechanical-gating or CICR. The muscles then contract through the sliding filament mechanism, causing shortening of sarcomeres and muscle contraction.

R-Type Calcium Channels

R-type voltage dependent calcium channels (VDCC) are involved in regulating calcium flow. The R-type VDCCs play an important role in decreased cerebral blood flow observed following SAH. Without being limited by theory, R-type voltage-dependent $Ca^{2+}$ channels that may be located within small diameter cerebral arteries may regulate global and local cerebral blood flow, since the concentration of intracellular free calcium ions determines the contractile state of vascular smooth muscle.

R-type voltage dependent calcium channel inhibitors are calcium entry blocking drugs whose main pharmacological effect is to prevent or slow the entry of calcium into cells via R-type voltage-gated calcium channels. The gene $Ca_v2.3$ encodes the principal pore-forming unit of R-type voltage-dependent calcium channels being expressed in neurons.

N-Type Calcium Channels

N-type ('N' for "Neural-Type") calcium channels are found primarily at presynaptic terminals and are involved in neurotransmitter release. Strong depolarization by an action potential causes these channels to open and allow influx of $Ca^{2+}$, initiating vesicle fusion and release of stored neurotransmitter. N-type calcium channels are blocked by ω-conotoxin.

P/Q-Type Calcium Channels

P-type ('P' for cerebellar Purkinje cells) calcium channels play a similar role to the N-type calcium channel in neurotransmitter release at the presynaptic terminal, and in neuronal integration in many neuronal types. They also are found in Purkinje fibers in the electrical conduction system of the heart (Llinás, R., et al. (1980). J. Physiol. (Lond.) 305: 171-95; Llinás, R. et al., (1989). Proc. Natl. Acad. Sci. U.S.A. 86 (5): 1689-93). Q-type calcium channel blockers appear to be present in cerebellar granule cells. They have a high threshold of activation and relatively slow kinetics.

T-Type Calcium Channels

T-type ('T' for transient) calcium channel blockers are low voltage-activated. They most often are found in neurons and cells that have pacemaker activity and in osteocytes. Mibefradil shows some selectivity for T-type over other types of VDCC.

Blockers and Inhibitors of Calcium Channels

Calcium channel blockers are a class of drugs and natural substances having effects on many excitable cells of the body, such as the muscle of the heart, smooth muscles of the vessels or neuron cells. The main action of calcium channel blockers is to decrease blood pressure.

Most calcium channel blockers decrease the force of contraction of the myocardium. This is known as the "negative inotropic effect" of calcium channel blockers. Most calcium channel blockers are not the preferred choice of treatment in individuals with cardiomyopathy due to their negative inotropic effects.

Many calcium channel blockers slow the conduction of electrical activity within the heart by blocking the calcium channel during the plateau phase of the action potential of the heart. This "negative dromotropic effect" causes a lowering of the heart rate and may cause heart blocks (which is known as the "negative chronotropic effect" of calcium channel blockers). The negative chronotropic effects of calcium channel blockers make them a commonly used class of agents for control of the heart rate in individuals with atrial fibrillation or flutter.

Calcium channel blockers act upon voltage-gated calcium channels (VGCCs) in muscle cells of the heart and blood vessels. By blocking the calcium channel they prevent large increases of the calcium levels in the cells when stimulated, which subsequently leads to less muscle contraction. In the heart, a decrease in calcium available for each beat results in a decrease in cardiac contractility. In blood vessels, a decrease in calcium results in less contraction of the vascular smooth muscle and therefore an increase in blood vessel diameter. The resultant vasodilation decreases total peripheral resistance, while a decrease in cardiac contractility decreases cardiac output. Since blood pressure is in part determined by cardiac output and peripheral resistance, blood pressure drops.

Calcium channel blockers do not decrease the responsiveness of the heart to input from the sympathetic nervous system. Since blood pressure regulation is carried out by the sympathetic nervous system (via the baroreceptor reflex), calcium channel blockers allow blood pressure to be maintained more effectively than do β-blockers. However, because calcium channel blockers result in a decrease in blood pressure, the baroreceptor reflex often initiates a reflexive increase in sympathetic activity leading to increased heart rate and contractility. The decrease in blood pressure also likely reflects a direct effect of antagonism of VDCC in vascular smooth muscle, leading to vasodilation. A β-blocker may be combined with a calcium channel blocker to minimize these effects.

The blockers for L, N, and P/Q-types of calcium channels are utilized in distinguishing channel subtypes. For the R-type calcium channel subtype, ω-agatoxin IIIA shows blocking activity, even though its selectivity is rather low. This peptide binds to all of the high voltage-activated channels including L, N, and P/Q subtypes (J. Biol. Chem., 275, 21309 (2000)). A putative R-type (or class α1E) selective blocker, SNX-482, is a 41 amino acid residue peptide with 3 disulfide linkages (1-4, 2-5 and 3-6 arrangement) (Biochemistry, 37, 15353 (1998), Peptides 1998, 748 (1999)). This peptide blocks the class E calcium channel ($IC_{50}$=15 nM to 30 nM) and R-type calcium current in the neurohypophysial nerve endings at 40 nM concentration. R-type (class E) calcium channel blocking activity is highly selective; no effect is observed on K+ and Na+ currents, and L, P/Q and T-type calcium currents. N-type calcium current is blocked only weakly 30-50% at 300 nM to 500 nM. Regionally, different sensitivity of R-type current to SNX-482 is observed; no significant effect on R-type current occurs in preparations of the neuronal cell body, retinal ganglion cells and hippocampal pyramidal cells. Using SNX-482, three α1E-calcium subunits with distinct pharmacological properties are recognized in cerebellar R-type calcium channels (J. Neurosci., 20, 171 (2000)). Similarly, it has been shown that secretion of oxytocin, but not vasopressin, is regulated by R-type calcium current in neurohypophysial terminals (J. Neurosci., 19, 9235 (1999)).

Dihydropyridine calcium channel blockers often are used to reduce systemic vascular resistance and arterial pressure, but are not used to treat angina (with the exception of amlodipine, which carries an indication to treat chronic stable angina as well as vasospastic angina) since the vasodilation and hypotension can lead to reflex tachycardia. This calcium channel blocker class is easily identified by the suffix "-dipine".

Phenylalkylamine calcium channel blockers are relatively selective for myocardium. They reduce myocardial oxygen demand and reverse coronary vasospasm. They have minimal vasodilatory effects compared with dihydropyridines. Their action is intracellular.

Benzothiazepine calcium channel blockers are an intermediate class between phenylalkylamine and dihydropyridines in their selectivity for vascular calcium channels. Benzothiazepines are able to reduce arterial pressure without producing the same degree of reflex cardiac stimulation caused by dihydropyridines due to their cardiac depressant and vasodilator actions.

L-type VDCC inhibitors are calcium entry blocking drugs whose main pharmacological effect is to prevent or slow entry of calcium into cells via L-type voltage-gated calcium channels. Examples of L-type calcium channel inhibitors include but are not limited to: dihydropyridine L-type blockers such as nisoldipine, nicardipine and nifedipine, AHF (such as 4aR,9aS)-(+)-4a-Amino-1,2,3,4,4a,9a-hexahydro-4aH-fluorene, HCl), isradipine (such as 4-(4-Benzofurazanyl)-1,-4-dihydro-2,6-dimethyl-3,5-pyridinedicarboxylic acid methyl 1-methhylethyl ester), Calciseptin/calciseptine (such as isolated from (*Dendroaspis polylepis polylepis*), H-Arg-Ile-Cys-Tyr-Ile-His-Lys-Ala-Ser-Leu-Pro-Arg-Ala-Thr-Lys-Thr-Cys-Val- Glu-Asn-Thr-Cys-Tyr-Lys-Met-Phe-Ile-Arg-Thr-Gln-Arg-Glu-Tyr-Ile-Ser-Glu-Arg-Gly-Cys- Gly-Cys-Pro-Thr-Ala-Met-Trp-Pro-Tyr-Gl-n-Thr-Glu-Cys-Cys-Lys-Gly-Asp-Arg-Cys-Asn-Lys-OH, Calcicludine (such as isolated from *Dendroaspis angusticeps* (eastern green mamba)), (H-Trp-Gln-Pro-Pro-Trp-Tyr-Cys-Lys-Glu-Pro-Val-Arg-Ile-Gly-Ser-Cys-Lys-Lys- Gln-Phe-Ser-Ser-P-he-Tyr-Phe-Lys-Trp-Thr-Ala-Lys-Lys-Cys-Leu-Pro-Phe-Leu-Phe-Ser-Gly- Cys-Gl-y-Gly-Asn-Ala-Asn-Arg-Phe-Gln-Thr-Ile-Gly-Glu-Cys-Arg-Lys-Lys-Cys-Leu-Gly-Lys-OH, Cilnidipine (such as also FRP-8653, a dihydropyridine-type inhibitor), Dilantizem (such as (2S,3S)-(+)-cis-3-Acetoxy-5-(2-dimethylaminoethyl)-2,3-dihydro-2-(4-methoxyphenyl)-1,5-benzothiazepin-4(5H)-one hydrochloride), diltiazem (such as benzothiazepin-4(5H)-one, 3-(acetyloxy)-5-[2-(dimethylamino)ethyl]-2,3-dihydro-2-(4-methoxyphenyl)-, (+)-cis-, monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from *Dendroaspis polylepis polylepis* venom), FTX-3.3 (such as an isolate from *Agelenopsis aperta*), Neomycin sulfate (such as $C_{23}H_{46}N_{60}O_{13}\cdot 3H_2SO_4$), Nicardipine (such as 1,4-Dihydro-2,6-dimethyl-4-(3-nitrophenyl)methyl-2-[methyl(phenylmethyl)a-mino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3 S,4aR,5R,6R)-[2,3,4,4a,5,6,7,8-Octahydro-3-(2-propenyl)-4a,5-dimethyl-2-o-xo-6-naphthyl] Z-3'-methylthio-1'-propenoate), Phloretin (such as 2',4',6'-Trihydroxy-3-(4-hydroxyphenyl)propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine (such as $C_2OH_{19}NO._5Cl$), SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (.+-.)-Methoxyverapamil or (+)-Verapamil (such as 5-[N-(3,4-Dimethoxyphenylethyl)methylamino]-2-(3,4-dimethoxyphenyl)-2-iso-propylvaleronitrile hydrochloride), and (R)-(+)-Bay K8644 (such as R-(+)-1,4-Dihydro-2,6-dimethyl-5-nitro-4-[2-(trifluoromethyl)phenyl]-3-py-ridinecarboxylic acid methyl ester). The foregoing examples may be specific to L-type voltage-gated calcium channels or may inhibit a broader range of voltage-gated calcium channels, e.g. N, P/Q, R, and T-type.

Endothelins

Endothelins are vasoconstricting peptides produced primarily in the endothelium. Endothelins increase blood pressure and vascular tone. This family of peptides includes endothelin-1 (ET-1), endothelin-2 (ET-2) and endothelin-3 (ET-3). These small peptides (21 amino acids) have an important role in vascular homeostasis. ET-1 is secreted mostly by vascular endothelial cells. The predominant ET-1 isoform is expressed in vasculature and is the most potent vasoconstrictor. ET-1 also has inotropic, chemotactic and mitogenic properties. It stimulates the sympathetic nervous system, and influences salt and water homeostasis through its effects on the renin-angiotensin-aldosterone system (RAAS), vasopressin and atrial natriuretic peptide. Endothelins are among the strongest vasoconstrictors known and have been implicated in vascular diseases of several organ systems, including the heart, general circulation and brain.

There are two key endothelin receptor types, $ET_A$ and $ET_B$. $ET_A$ and $ET_B$ have distinct pharmacological characteristics. The $ET_A$-receptor affinity is much higher for ET-1 than for ET-3. $ET_A$-receptors are located in the vascular smooth muscle cells, but not in endothelial cells. The binding of endothelin to $ET_A$ increases vasoconstriction and the retention of sodium, leading to increased blood pressure. $ET_B$ receptors primarily are located on the endothelial cells that line the interior of the blood vessels. Endothelin binding to $ET_B$ receptors lowers blood pressure by increasing natriuresis and diuresis, and releasing nitric oxide. ET-1 and ET-3 activate the $ET_B$-receptor equally, which in turn leads to vasodilation via production of NO and prostaglandins. Endothelin-1 (1-31) also has been demonstrated to cause vascular smooth muscle constriction via $ET_A$-receptor stimulation and to induce NO production in endothelial cells via $ET_B$-receptors. Some $ET_B$-receptors are located in vascular smooth muscle, where they may mediate vasoconstriction. A number of endothelin receptors are regulated by various factors. Angiotensin II and phorbol esters down-regulate endothelin receptors whereas ischemia and cyclosporin increase the number of endothelin receptors.

A number of peptide and nonpeptide ET antagonists have been studied. $ET_A$-receptor antagonists may include, but are not limited to, A-127722 (non-peptide), ABT-627 (non-peptide), BMS 182874 (non-peptide), BQ-123 (peptide), BQ-153 (peptide), BQ-162 (peptide), BQ-485 (peptide), BQ-518 (peptide), BQ-610 (peptide), EMD-122946 (non-peptide), FR 139317 (peptide), IPI-725 (peptide), L-744453 (non-peptide), LU 127043 (non-peptide), LU 135252 (non-peptide), PABSA (non-peptide), PD 147953 (peptide), PD 151242 (peptide), PD 155080 (non-peptide), PD 156707 (non-peptide), RO 611790 (non-peptide), SB-247083 (non-peptide), clazosentan (non-peptide), atrasentan (non-peptide), sitaxsentan sodium (non-peptide), TA-0201 (non-peptide), TBC 11251 (non-peptide), TTA-386 (peptide), WS-7338B (peptide), ZD-1611 (non-peptide), and aspirin (non-peptide). $ET_{A/B}$-receptor antagonists may include, but are not limited to, A-182086 (non-peptide), CGS 27830 (non-peptide), CP 170687 (non-peptide), J-104132 (non-peptide), L-751281 (non-peptide), L-754142 (non-peptide), LU 224332 (non-peptide), LU 302872 (non-peptide), PD 142893 (peptide), PD 145065 (peptide), PD 160672 (non-peptide), RO-470203 (bosentan, non-peptide), RO 462005 (non-peptide), RO 470203 (non-peptide), SB 209670 (non-peptide), SB 217242 (non-peptide), and TAK-044 (peptide). $ET_B$-receptor antagonists may include, but are not limited to, A-192621 (non-peptide), A-308165 (non-peptide), BQ-788 (peptide), BQ-017 (peptide), IRL 1038 (peptide), IRL 2500 (peptide), PD-161721 (non-peptide), RES 701-1 (peptide), and RO 468443 (peptide).

ET-1 is translated initially to a 212 amino-acid peptide (pre-proendothelin-1). It is further converted to proendothelin-1 after removal of the secretory sequence. Proendothelin-1 then is cleaved by furin to generate the biologically-inactive precursor big endothelin-1. Mature ET-1 is formed upon cleavage of big endothelin-1 by one of several endothelin-converting enzymes (ECEs). There are two splice variants of ECE-1; these are ECE-1a and ECE-1b. Each has functionally distinct roles and tissue distribution. ECE-1a is expressed in the Golgi network of endothelin-producing cells and cleaves big endothelin-1 to form ET-1. ECE-1b is localized at the plasma membrane and cleaves extracellular big endothelin-1. Both ECE-1a and ECE-1b are inhibited by metalloprotease inhibitor phosphoramidon. ECEs also are located on α-actin filaments in smooth muscle cells. ECE inhibition by phosphoramidon completely blocks vasoconstriction to big endothelin-1. ECE inhibitors may include, but are not limited to, B-90063 (non-peptide), CGS 26393 (non-peptide), CGS 26303 (non-peptide), CGS 35066 (non-peptide), phosphoramidon (peptide), PP-36 (peptide), SM-19712 (non-peptide), and TMC-66 (non-peptide).

In a healthy individual, a delicate balance between vasoconstriction and vasodilation is maintained by endothelin and other vasoconstrictors on the one hand and nitric oxide, prostacyclin and other vasodilators on the other. Endothelin anatagonists may have a role in the treatment of cardiac, vascular and renal diseases associated with regional or systemic vasoconstriction and cell proliferation, such as essential hypertension, pulmonary hypertension, chronic heart failure and chronic renal failure.

Transient Receptor Potential Channels

The transient receptor potential (TRP) channel family is a member of the calcium channel group. These channels include transient receptor potential protein and homologues thereof, the vanilloid receptor subtype I, stretch-inhibitable non-selective cation channel, olfactory, mechanosensitive channel, insulin-like growth factor I-regulated calcium channel, and vitamin D-responsive apical, epithelial calcium channel (ECaC). Each of these molecules is at least 700 amino acids in length, and shares certain conserved structural features. Predominant among these structural features are six transmembrane domains, with an additional hydrophobic loop present between the fifth and sixth transmembrane domains. It is believed that this loop is integral to the activity of the pore of the channel formed upon membrane insertion. TRP channel proteins also include one or more ankyrin domains and frequently display a proline-rich region at the N-terminus.

Transient receptor potential (TRP) cation channels are present in vascular smooth muscle and are involved in the smooth muscle depolarizing response to stimuli such as membrane stretch. Uridine triphosphate (UTP) invokes membrane depolarization and constriction of vascular smooth muscle by activating a cation current that exhibits inward rectification, is not rapidly desensitized, and is blocked by $Gd^{3+}$. Canonical transient receptor potential (TRPC) proteins form $Ca^{2+}$ permeable, non-selective cation channels in a variety of mammalian tissues. Suppression of one member of this family of channels, TRPC6, has been reported to prevent an α1-adenoreceptor-activated cation current in cultured rabbit portal vein myocytes. However, suppression of TRPC6 channels in cerebral vascular smooth muscle does not attenuate the UTP-induced membrane depolarization and vasoconstriction. In contrast, TRPC3, unlike TRPC6, has been found to mediate the agonist induced depolarization, as observed in rat cerebral artery, following UTP activation of the P2Y receptor. Thus, TRPC3 channels in vascular smooth muscle mediate agonist-induced depolarization which contributes to vasoconstriction in resistance-sized cerebral arteries.

The TRP1 channel family comprises a large group of channels mediating an array of signal and sensory transduction pathways. The proteins of the mammalian TRPC subfamily are the products of at least seven genes coding for cation channels that appear to be activated in response to PLC-coupled receptors. The putative ion channel subunits TRPC3, TRPC6, and TRPC7 comprise a structurally related subgroup of the family of mammalian TRPC channels. The ion channels formed by these proteins appear to be activated downstream of phospholipase C (PLC). PLC-dependent activation of TRPC6 and TRPC7 has been shown to involve diacylglycerol and is independent of G proteins or inositol 1,4,5-triphosphate (IP3).

TRPC channels are widely expressed among cell types and may play important roles in receptor-mediated $Ca^{2+}$ signaling. The TRPC3 channel is known to be a $Ca^{2+}$ conducting channel activated in response to phospholipase C-coupled receptors. TRPC3 channels have been shown to interact directly with intracellular inositol 1,4,5-trisphosphate receptors ($InsP_{3Rs}$) and that channel activation is mediated through coupling to $InsP_{3Rs}$.

Agents useful for increasing arterial blood flow, inhibiting vasoconstriction or inducing vasodilation are agents that inhibit TRP channels. These inhibitors embrace compounds that are TRP channel antagonists. Such inhibitors are referred to as activity inhibitors or TRP channel activity inhibitors. As used herein, the term "activity inhibitor" refers to an agent that interferes with or prevents the activity of a TRP channel. An activity inhibitor may interfere with the ability of the TRP channel to bind an agonist such as UTP. An activity inhibitor may be an agent that competes with a naturally occurring activator of TRP channel for interaction with the activation binding site on the TRP channel. Alternatively, an activity inhibitor may bind to the TRP channel at a site distinct from the activation binding site, but in doing so, it may, for example, cause a conformational change in the TRP channel, which is transduced to the activation binding site, thereby precluding binding of the natural activator. Alternatively, an activity inhibitor may interfere with a component upstream or downstream of the TRP channel but which interferes with the activity of the TRP channel. This latter type of activity inhibitor is referred to as a functional antagonist. Non-limiting examples of a TRP channel inhibitor that is an activity inhibitor are gadolinium chloride, lanthanum chloride, SKF 96365 and LOE-908.

Current treatments to prevent or reduce cerebral vasospasm consists of measures to prevent or minimize secondary brain injury, use calcium channel blockers, hemodynamic management and endovascular therapies. Therapy often is initiated prophylactically in patients and may include: (in stage 1) hemodynamic stabilization including maintaining normovolemia, managing blood pressure, and orally-administered L-type voltage-gated calcium channel antagonists; and (in stage 2) further hemodynamic manipulation or infusion of vasodilator drugs into vasospastic arteries or dilating them with balloons. However, the aforementioned treatments are expensive, time consuming and only partially effective.

For over 35 years, physicians have been trying to prevent or reduce the incidence of vasospasm and have had limited effect due to side effects of current agents or lack of efficacy. There are currently no FDA approved agents for the prevention of vasospasm or the reduction in delayed ischemic neurologic deficits also known as delayed cerebral ischemia (DCI). Current methods to prevent vasospasm have failed due to lack of efficacy or safety issues, primarily hypotension and cerebral edema. Currently, the only FDA-approved available agent is Nimodipine which does not reduce vasospasm, though it improved outcomes in SAH patients.

Voltage-gated calcium channel antagonists may be effective at preventing and reversing vasospasm to a certain extent, however, prior art treatments administer doses too low to exert a maximal pharmacologic effect. Endothelin-receptor antagonists also may be effective at preventing and reversing vasospasm to a certain extent, but this reversal or prevention of vasospasm does not translate into as marked an improvement in outcome as would be anticipated by the reduction in vasospasm. Without being limited by theory, it is postulated the systemic delivery of the voltage-gated calcium channel antagonists and endothelin antagonist drugs may cause side effects that mitigate the beneficial effects on vasospasm, such as, for example, systemic hypotension and pulmonary vasodilation with pulmonary edema, which prevent the administration of higher systemic doses. Dilation of blood vessels in the lungs also may cause lung edema and lung injury.

Experimental evidence strongly supports a role both for the influx of calcium through voltage-gated calcium channels and for endothelin-mediated contraction as a primary underlying mechanism responsible for vasospasm. Alternately, the contraction may be due to calcium influx through putative transient receptor potential proteins and blocking these channels also may prevent or reverse vasospasm.

Accordingly, there is a need for a delivery system and/or methods that prevent cerebral vasospasm or reduce the severity of cerebral vasospasm.

SUMMARY

The present invention relates to a delivery system of compounds targeting at least one cerebral artery to prevent and/or reduce the occurrence of or severity of cerebral vasospasm, and or constriction of at least one cerebral artery due to other conditions, such as head injury, atherosclerosis, or stenosis after angioplasty and stenting. In one aspect, the present invention provides a method of treating a cerebral vasospasm in a human, the method comprising the steps: a) providing a pharmaceutical composition; b) administering a therapeutically effective amount of the pharmaceutical composition to a predetermined location in close proximity to a cerebral artery within a subarachnoid space; c) wherein the pharmaceutical composition produces a localized pharmacologic effect thereby treating the cerebral vasospasm. According to one embodiment of the method, the pharmaceutical composition comprises a therapeutic agent and a pharmaceutical carrier. According to another embodiment, the therapeutic agent is a calcium channel blocker. According to another embodiment, the therapeutic agent is a calcium channel antagonist. According to another embodiment, the therapeutic agent is a calcium channel inhibitor. According to another embodiment, the therapeutic agent is a transient receptor potential protein blocker. According to another embodiment, the therapeutic agent is an endothelin receptor. According to another embodiment, the carrier is a gel compound. According to another embodiment, the carrier is a semisolid compound. According to another embodiment, the carrier is a slow-release solid compound. According to another embodiment, the therapeutic agent is selected from the group consisting of amlodipine, aranidipine, azelnidipine, bamidipine, benidipine, bepridil, cinaldipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, verapamil or a combination thereof. According to another embodiment, the therapeutic agent is selected from the group consisting of A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL 2500, PD-161721, RES 701-1, and RO 468443. According to another embodiment, the therapeutic agent is selected from the group consisting of SKF 96365 and LOE 908. According to another embodiment, the predetermined location in step (b) is from about 0.001 mm to about 10 mm from a cerebral artery. According to another embodiment, the pharmaceutical composition is administered by surgical injection. According to another embodiment, the pharmaceutical composition is administered by implantation. In another aspect, the present invention provides a method of treating a human for vasospasm after subarachnoid hemorrhage in at least one cerebral artery, the method comprising the steps of: a) providing a pharmaceutical composition; b) administering a therapeutically effective amount of the pharmaceutical composition to a predetermined location in close proximity to a cerebral artery within a subarachnoid space; c) wherein the pharmaceutical composition produces a localized therapeutic effect thereby treating the vasospasm. In one embodiment of the method, the pharmaceutical composition comprises a therapeutic agent and pharmaceutical carrier. According to another embodiment, the therapeutic agent is a calcium channel blocker. According to another embodiment, the therapeutic agent is a calcium channel antagonist. According to another embodiment, the therapeutic agent is a calcium channel inhibitor. According to another embodiment, the therapeutic agent is a transient receptor potential protein blocker. According to another embodiment, the therapeutic agent is an endothelin receptor antagonist. According to another embodiment, the carrier is a gel compound. According to another embodiment, the carrier is a semisolid compound. According to another embodiment, the carrier is a slow-release solid compound. According to another embodiment, the therapeutic agent is selected from the group consisting of amlodipine, aranidipine, azelnidipine, bamidipine, benidipine, bepridil, cinaldipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, verapamil or a combination thereof. According to another embodiment, the therapeutic agent is selected from the group consisting of A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL 2500, PD-161721, RES 701-1, and RO 468443. According to another embodiment, the therapeutic agent is selected from the group consisting of SKF 96365 and LOE 908. According to another embodiment, the predetermined location in step (b) is from about 0.001 mm to about 10 mm from a cerebral artery. According to one embodiment, the pharmaceutical composition is administered by implantation. According to another embodiment, the pharmaceutical composition is administered by surgical injection.

In another aspect, the present invention provides a pharmaceutical composition for administration into the subarachnoid space for treating cerebral vasospasm in a human comprising a) a therapeutically effective amount of a therapeutic agent; and b) a pharmaceutical carrier. In one embodiment of the method, the therapeutic agent is selected from the group consisting of amlodipine, aranidipine, azelnidipine, bamidipine, benidipine, bepridil, cinaldipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, verapamil, A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL 2500, PD-161721, RES 701-1, RO 468443, SKF 96365 and LOE 908. According to another embodiment, the therapeutic agent is a calcium channel blocker. According to another embodiment, the therapeutic agent is a calcium channel antagonist. According to another embodiment, the therapeutic agent is a calcium channel inhibitor. According to another embodiment, the therapeutic agent is a transient receptor potential protein blocker. According to another embodiment, the therapeutic agent is an endothelin receptor antagonist. According to another embodiment, the pharmaceutical carrier is a gel compound. According to another embodiment, the pharmaceutical carrier is a slow-release solid compound. According to another embodiment, the pharmaceutical carrier is a semisolid compound.

DETAILED DESCRIPTION OF THE INVENTION

Figure 1:
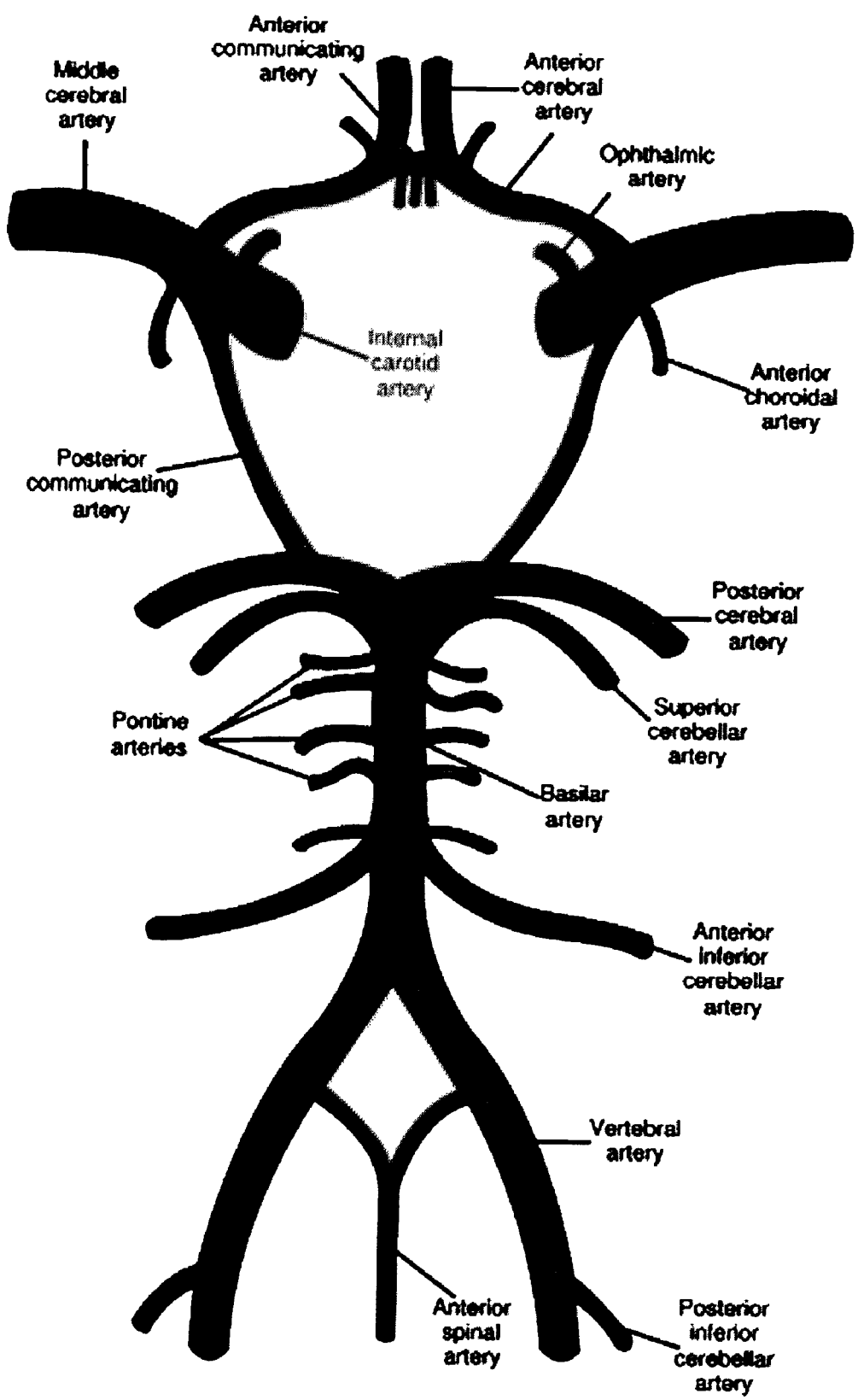
FIG. 1 shows an illustrative view of the cerebral arteries.

The present invention relates to a delivery system of therapeutic agents that are delivered to the cerebral arteries to prevent or reduce the severity of cerebral vasospasm. More specifically, the present invention relates to a delivery system to the cerebral arteries of the pharmaceutical agents that prevent or reduce the severity of cerebral vasospasm. As opposed to prior art treatments previously studied, including intravenous and intraarterial delivery, the present invention provides for delivery of therapeutic agents to a particular area around the cerebral arteries that effectuates a localized release of the pharmacologic agents and leads to better outcomes by the reduction of delayed cerebral ischemia (DCI) caused by cerebral vasospasm. In one aspect, the present invention provides use of a transient receptor potential protein blocker as the active agent that blocks channels believed to be alternate pathways activated in the development of vasospasm.

In one aspect, the present invention is an improved method of utilizing calcium channel blockers or calcium channel inhibitors, or calcium channel antagonists, or endothelin receptor antagonists, or transient receptor potential proteins to prevent or reduce the severity of cerebral vasospasm. The term "antagonist" as used herein refers to a substance that counteracts the effects of another substance. The term "agonist" as used herein refers to a chemical substance capable of activating a receptor to induce a full or partial pharmacological response. The term "blocker" as used herein refers to a substance that inhibits the physiological action of another substance. The term "transient receptor potential protein blocker" as used herein refers to a protein that is structurally distinct from other calcium channel blockers and that blocks intracellular calcium increases in cells due to receptor-mediated calcium influx. The term "transient receptor potential protein antagonist" as used herein refers to a protein that is structurally distinct from other calcium channel antagonists and that antagonizes intracellular calcium increases in cells due to receptor-mediated calcium influx. Transient receptor potential protein blockers and antagonists include, but are not limited to, SK&F 96365 (1-(beta-[3-(4-methoxy-phenyl)propoxy]-4-methoxyphenethyl)-1H-imidazole hydrochloride) and LOE 908 (RS)-(3,4-dihydro-6,7-dimethoxyisoquinoline-1-gamma 1)-2-phenyl-N,N-di-[2-(2,3,4-trimethoxyphenyl)ethyl]acetamide).

In another aspect, the present invention provides methods to prevent or reduce the severity of cerebral vasospasm. In one embodiment, the method comprises the step of administering a therapeutically effective amount of a calcium channel blocker in the subarachnoid space at a predetermined location in close proximity to a cerebral artery. In another embodiment, the method comprises the step of administering a therapeutically effective amount of a calcium channel inhibitor in the subarachnoid space at a predetermined location in close proximity to a cerebral artery. In another embodiment, the method comprises the step of administering a therapeutically effective amount of a calcium channel antagonist in the subarachnoid space at a predetermined location in close proximity to a cerebral artery. In another embodiment, the method comprises the step of administering a therapeutically effective amount of a transient receptor potential protein blocker in the subarachnoid space at a predetermined location in close proximity to a cerebral artery. In another embodiment, the method comprises the step of administering a therapeutically effective amount of an endothelin receptor antagonist in the subarachnoid space at a predetermined location in close proximity to a cerebral artery.

As shown in FIG. 1, the term "cerebral arteries" refers to at least one of the anterior communication artery, middle cerebral artery, internal carotid artery, anterior cerebral artery, ophthalmic artery, anterior choroidal artery, posterior communicating artery, and basilar artery, and vertebral artery among others. The phrase "in close proximity" as used herein refers to in the subarachnoid space within about 0.001 mm to about 10 mm of the said arteries. In each of these embodiments, it is desired that the therapeutically effective amount of the pharmaceutical agent is implanted in the subarachnoid space and/or placed in close proximity to a cerebral artery or arteries.

The term "therapeutically effective amount" or an "amount effective" of one or more of the active agents is an amount that is sufficient to provide the intended benefit of treatment. An effective amount of the active agents that can be employed ranges from generally 0.1 mg/kg body weight and about 50 mg/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a surgeon using standard methods.

The term "therapeutic agent" as used herein refers to a drug, molecule, nucleic acid, protein, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably. The active agent may be a calcium channel inhibitor, a calcium channel antagonist, a calcium channel blocker, a transient receptor potential protein blocker, or an endothelin anatagonist.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "drug" as used herein refers to a therapeutic agent or any substance, other than food, used in the prevention, diagnosis, alleviation, treatment, or cure of disease.

The term "treat" or "treating" as used herein refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously symptomatic for the disorder(s).

The term "reduce" or "reducing" as used herein refers to limit occurrence of the disorder in individuals at risk of developing the disorder.

The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be locally administered by means such as, but not limited to, injection, implantation, grafting, topical application, or parenterally.

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The term "topical" refers to administration of a composition at, or immediately beneath, the point of application. The phrase "topically applying" describes application onto one or more surfaces(s) including epithelial surfaces. Although topical administration, in contrast to transdermal administration, generally provides a local rather than a systemic effect. The terms "topical administration" and "transdermal administration" as used herein, unless otherwise stated or implied, are used interchangeably.

The term "disease" or "disorder", as used herein, refers to an impairment of health or a condition of abnormal functioning. The term "syndrome," as used herein, refers to a pattern of symptoms indicative of some disease or condition. The term "injury," as used herein, refers to damage or harm to a structure or function of the body caused by an outside agent or force, which may be physical or chemical. The term "condition", as used herein, refers to a variety of health states and is meant to include disorders or diseases caused by any underlying mechanism or disorder, injury, and the promotion of healthy tissues and organs.

The term "modulate" as used herein means to regulate, alter, adapt, or adjust to a certain measure or proportion.

The terms "subject" or "individual" or "patient" are used interchangeably to refer to a member of an animal species of mammalian origin, including humans.

The term "hypertension" as used herein refers to high systemic blood pressure; transitory or sustained elevation of systemic blood pressure to a level likely to induce cardiovascular damage or other adverse consequences.

The term "hypotension" as used herein refers to subnormal systemic arterial blood pressure; reduced pressure or tension of any kind.

The term "subarachnoid hemorrhage" or "SAH" is used herein to refer to a condition in which blood collects beneath the arachnoid mater. This area, called the subarachnoid space, normally contains cerebrospinal fluid. The accumulation of blood in the subarachnoid space may lead to stroke, seizures, and other complications. Additionally, SAH may cause permanent brain damage and a number of harmful biochemical events in the brain. Causes of SAH include bleeding from a cerebral aneurysm, vascular anomaly, trauma and extension into the subarachnoid space from a primary intracerebral hemorrhage. Symptoms of SAH include, for example, sudden and severe headache, nausea and/or vomiting, symptoms of meningeal irritation (e.g., neck stiffness, low back pain, bilateral leg pain), photophobia and visual changes, and/or loss of consciousness. SAH is often secondary to a head injury or a blood vessel defect known as an aneurysm. In some instances, SAH can induce cerebral vasospasm that may in turn lead to an ischemic stroke. A common manifestation of a SAH is the presence of blood in the CSF. Subjects having a SAH may be identified by a number of symptoms. For example, a subject having a subarachnoid hemorrhage will present with blood in the subarachnoid, usually in a large amount. Subjects having a subarachnoid hemorrhage can also be identified by an intracranial pressure that approximates mean arterial pressure, by a fall in cerebral perfusion pressure, or by the sudden transient loss of consciousness (sometimes preceded by a painful headache). In about half of cases, subjects present with a severe headache which may be associated with physical exertion. Other symptoms associated with subarachnoid hemorrhage include nausea, vomiting, memory loss, hemiparesis and aphasia. Subjects having a SAH also may be identified by the presence of creatine kinase-BB isoenzyme activity in their CSF. This enzyme is enriched in the brain but normally is not present in the CSF. Thus, its presence in the CSF is indicative of "leak" from the brain into the subarachnoid space. Assay of creatine-kinase BB isoenzyme activity in the CSF is described by Coplin et al. (Coplin et al 1999 Arch Neurol 56, 1348-1352) Additionally, a spinal tap or lumbar puncture may be used to demonstrate whether blood is present in the CSF, a strong indication of a subarachnoid hemorrhage. A cranial CT scan or an MRI also may be used to identify blood in the subarachnoid region. Angiography also may be used to determine not only whether a hemorrhage has occurred, but also the location of the hemorrhage. Subarachnoid hemorrhage commonly results from rupture of an intracranial saccular aneurysm or from malformation of the arteriovenous system in, and leading to, the brain. Accordingly, a subject at risk of having a subarachnoid hemorrhage includes a subject having a saccular aneurysm as well as a subject having a malformation of the arteriovenous system. Common sites of saccular aneurysms are the top of the basilar artery and the junction of the basilar artery with the superior cerebellar or the anterior inferior cerebellar artery. Subjects having a subarachnoid hemorrhage may be identified by an eye examination, whereby slowed eye movement may indicate brain damage. A subject with a saccular aneurysm may be identified through routine medical imaging techniques, such as CT and MRI. A saccular or cerebral aneurysm forms a mushroom-like or berry-like shape (sometimes referred to as "a dome with a neck" shape).

The term "vasospasm" as used herein refers to a sudden decrease in the internal diameter of a cerebral artery that results from contraction of smooth muscle within the wall of the artery which causes a decrease in blood flow, but generally without an increase in systemic vascular resistance. Vasospasm results in decreased cerebral blood flow and increased cerebral vascular resistance. Without being limited by theory, it generally is believed that vasospasm is caused by local injury to vessels, such as that which results from atherosclerosis and other structural injury including traumatic head injury, aneurismal subarachnoid hemorrhage and other causes of subarachnoid hemorrhage. Cerebral vasospasm is a naturally occurring vasoconstriction that also may be triggered by the presence of blood in the CSF, a common occurrence after rupture of an aneurysm or following traumatic head injury. Cerebral vasospasm ultimately can lead to brain cell damage, in the form of cerebral ischemia and infarction, due to interrupted blood supply. The term "cerebral vasospasm" as used herein refers to the delayed occurrence of narrowing of large capacitance arteries at the base of the brain after subarachnoid hemorrhage, often associated with diminished perfusion in the territory distal to the affected vessel. Cerebral vasospasm may occur any time after rupture of an aneurysm but most commonly peaks at seven days following the hemorrhage and often resolves within 14 days when the blood has been absorbed by the body.

The phrase "a subject having a vasospasm" as used herein refers to a subject who presents with diagnostic markers and symptoms associated with vasospasm. Diagnostic markers include, but are not limited to, the presence of blood in the CSF and/or a recent history of a subarachnoid hemorrhage. Vasospasm associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly. The phrase "a subject having a cerebral vasospasm" as used herein refers to one who has symptoms of or has been diagnosed with cerebral vasospasm.

A subject at risk of cerebral vasospasm is one who has one or more predisposing factors to the development of cerebral vasospasms. A predisposing factor includes, but is not limited to, existence of a subarachnoid hemorrhage. A subject who has experienced a recent SAH is at significantly higher risk of developing cerebral vasospasm than a subject who has not had a recent SAH. MR angiography, CT angiography and catheter angiography can be used to diagnose cerebral vasospasm. Angiography is a technique in which a contrast agent is introduced into the blood stream in order to view blood flow and/or arteries. A contrast agent is required because blood flow and/or arteries sometimes are only weakly apparent in a regular MR scan, CT scan or radiographic film for catheter angiography. Appropriate contrast agents will vary depending upon the imaging technique used. For example, gadolinium is commonly used as a contrast agent used in MR scans. Other MR appropriate contrast agents are known in the art.

Transcranial Doppler ultrasound also may be used to diagnose and monitor the progression of a vasospasm. As mentioned earlier, the presence of blood in the cerebrospinal fluid may be detected using CT scans. However, in some instances where the amount of blood is so small as to not be detected by CT, a lumbar puncture is warranted. A subject at risk of a vasospasm includes a subject who has detectable blood in the cerebrospinal fluid, or one who has a detectable aneurysm as detected by a CT scan, yet has not begun to experience the symptoms associated with having a vasospasm. A subject at risk of a vasospasm also may be one who has experienced a traumatic head injury. Traumatic head injury usually results from a physical force to the head region, in the form of a fall or a forceful contact with a solid object. Subjects at risk of a vasospasm also may include those who have recently (e.g., in the last two weeks or months) experienced a subarachnoid hemorrhage.

The calcium channel inhibitors, antagonists, and blockers described herein are isolated molecules. An isolated molecule is a molecule that is substantially pure and is free of other substances with which it is ordinarily found in nature or in vivo systems to an extent practical and appropriate for its intended use. In particular, the calcium channel inhibitors, antagonists, and blockers are sufficiently pure and are sufficiently free from other biological constituents of host cells so as to be useful in, for example, producing pharmaceutical preparations or sequencing if the calcium channel inhibitor, antagonist, or blocker is a nucleic acid, peptide, or polysaccharide. Because calcium channel inhibitors, calcium channel blockers, or calcium channel antagonists may be admixed with a pharmaceutically-acceptable carrier in a pharmaceutical preparation, the calcium channel inhibitors, calcium channel blockers, or calcium channel antagonists may comprise only a small percentage by weight of the preparation. The calcium channel inhibitor, calcium channel blocker, or calcium channel antagonist is nonetheless substantially pure in that it has been substantially separated from the substances with which it may be associated in living systems or during synthesis.

In one aspect of the invention, a calcium channel inhibitor is administered to the subject having a vasospasm or at risk of having a vasospasm in a therapeutically effective amount to treat the vasospasm. A therapeutically effective amount to treat vasospasm may be that amount necessary to ameliorate, reduce or eliminate altogether one or more symptoms relating to a vasospasm, preferably including brain damage that results from vasospasm, such as an infarct. Brain damage may be measured anatomically using medical imaging techniques to measure infarct sizes. Alternatively or in conjunction, brain damage may be measured functionally in terms of cognitive, sensory or motor or other skills of the subject. In another embodiment, a calcium channel blocker is administered to the subject having or at risk of having a vasospasm in a therapeutically effective amount to treat the vasospasm. In another embodiment, a calcium channel antagonist is administered to the subject having or at risk of having a vasospasm in a therapeutically effective amount to treat the vasospasm. In another embodiment, a transient receptor potential protein blocker is administered to the subject having or at risk of having a vasospasm in a therapeutically effective amount to treat the vasospasm. In another embodiment, an endothelin antagonist is administered to the subject having or at risk of having a vasospasm a therapeutically effective amount to treat or prevent the vasospasm.

Inhibitors may be combined with other therapeutic agents, such as an anti-hypertensive agent and/or an anti-cerebral vasospasm agent and administered locally. The inhibitor and other therapeutic agent may be administered simultaneously or sequentially. When the other therapeutic agents are administered simultaneously, they can be administered in the same or separate formulations, but are administered at the same time. The other therapeutic agents are administered sequentially with one another and with inhibitor when the administration of the other therapeutic agents and the inhibitor is temporally separated. The separation in time between the administration of these agents may be a matter of minutes or it may be longer. The therapeutic agents may be a calcium channel antagonist, a calcium channel blocker, a transient receptor potential protein blocker, or an endothelin antagonist.

The calcium channel blockers, calcium channel inhibitors, or calcium channel antagonists may be effective against voltage-gated calcium channels, including L-type calcium channels, R-type calcium channels, N-type calcium channels, P/Q-type calcium channels and T-type calcium channels. They include any of a number of effective pharmaceutical agents, including, but not limited to, amlodipine, aranidipine, azelnidipine, bamidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, verapamil or a combination thereof.

In one aspect, the present invention provides a delivery system of the calcium channel antagonist nimodipine. Nimodipine has a high potency, long enough half life to last the required 7-10 days, and appropriate lipid solubility. When surgically implanted at therapeutically effective dosages, it can prevent vasospasm without unwanted side effects.

In another aspect, the present invention provides a delivery system for the endothelin receptor antagonist clazosentan. Clazosentan has a high potency for contractile endothelin receptors on cerebral arteries. When surgically implanted at therapeutically effective dosages, it can prevent vasospasm without unwanted side effects.

In another aspect, the present invention provides a delivery system of the endothelin receptor antagonist atrasentan. Atrasentan has a high potency for contractile endothelin receptors on cerebral arteries and a long enough half life to last the required 7-10 days. When surgically implanted at therapeutically effective dosages, it can prevent vasospasm without unwanted side effects.

In another aspect, the present invention provides a delivery system of the transient receptor potential antagonist SKF 96365. SKF 96365 has a high potency for nonselective cation channels that comprise in part transient receptor potential proteins on cerebral arteries. When surgically implanted at therapeutically effective dosages, it can prevent vasospasm without unwanted side effects.

In another aspect, the present invention provides a delivery system of the transient receptor potential antagonist LOE 908. LOE 908 has a high potency for nonselective cation channels that comprise in part transient receptor potential proteins on cerebral arteries. When surgically implanted at therapeutically effective dosages, it can prevent vasospasm without unwanted side effects.

In another aspect, the present invention provides a delivery system of the calcium channel antagonist clevidipine. Clevidipine is rapidly metabolized by plasma esterases and when surgically implanted at therapeutically effective dosages, can prevent vasospasm without unwanted side effects. Since clevidipine is metabolized via plasma esterases, the incidence of systemic side effects, principally hypotension should be reduced or eliminated.

In another aspect, the present invention provides a delivery system of the calcium channel antagonist nimodipine.

In another embodiment, the present invention provides a method of preventing or reducing the severity of cerebral vasospasm comprising the step of implanting a gel, slow-release solid or semisolid compound, optionally as a sustained release gel, slow-release solid or semisolid compound, the gel, slow-release solid or semisolid compound comprising a therapeutically effective amount of an active agent and a coating. The active ingredient may be any of the aforementioned calcium channel antagonists, calcium channel inhibitors, calcium channel blockers, transient receptor potential protein blockers, or endothelin antagonists. In some such embodiments, the calcium channel antagonist is nicardipine or nimodipine. In some such embodiments, the calcium channel antagonist is clevidipine. In some such embodiments, the calcium channel antagonist is nimodipine. In some such embodiments, the active ingredient is a transient receptor potential protein blocker. In some such embodiments, the transient receptor potential protein blocker is SKF 96365. In some such embodiments, the transient receptor potential protein blocker is LOE 908. In some such embodiments, the active ingredient is an endothelin antagonist. In some such embodiments, the endothelin antagonist is clazosentan. In some such embodiments, the endothelin antagonist is atrasentan. The coating can be of any desired material, preferably a polymer or mixture of different polymers. Optionally, the polymer may be utilized during the granulation stage to form a matrix with the active ingredient so as to obtain a desired release pattern of the active ingredient. The gel, slow-release solid or semisolid compound is capable of releasing of the active agent over a desired period of time. The gel, slow-release solid or semisolid compound is implanted in close proximity to a cerebral artery, whereby the release of the active agent produces a localized pharmacologic effect.

In another embodiment of the method, the method comprises the step of implanting surgically or injecting a nicardipine gel, nicardipine slow-release solid or nicardipine semisolid compound is implanted surgically or injected into the patient to deliver drug substance at the site of vasospasm. Because the nicardipine gel, nicardipine slow-release solid or nicardipine semisolid agent is delivered specifically (locally) to the site, the dosage required to prevent vasospasm will be appropriate, to reduce, prevent or circumvent the main side effect that prevents the administration of higher systemic doses, e.g., hypotension. In addition, due to the high potency, optimal half life, and appropriate lipid solubility characteristics of nicardipine, it is desired to deliver efficacious amounts of this agent to a specific site (without unwanted side effects). This also would be the case for a transient receptor potential protein blocker or an endothelin antagonist.

In another embodiment, the method comprises the step of implanting surgically or injecting a clevidipine gel, clevidipine slow-release solid or clevidipine semisolid agent to deliver drug substance at the site of vasospasm. Because the clevidipine gel, clevidipine slow-release solid or clevidipine semisolid compound are delivered specifically (locally) to the site, the dosage required to prevent vasospasm will be appropriate, and can reduce, prevent or circumvent the main side effect that prevents the administration of higher systemic doses, e.g., hypotension. In addition, due to the high potency, optimal half life, and appropriate lipid solubility characteristics of clevidipine, it is desired to deliver efficacious amounts of this drug to a specific site (without unwanted side effects).

In another embodiment, the method comprises the step of implanting surgically or injecting a nimodipine gel, nimodipine slow-release solid or clevidipine semisolid agent to deliver drug substance at the site of vasospasm. Because the nimodipine gel, nimodipine slow-release solid or clevidipine semisolid compound are delivered locally to the site, the dosage required to prevent vasospasm will be appropriate, and can reduce, prevent or circumvent the main side effect that prevents the administration of higher systemic doses, e.g., hypotension.

In another embodiment, the method comprises the step of implanting surgically or injecting a transient receptor potential protein blocker gel, transient receptor potential protein blocker slow-release solid or transient receptor potential protein blocker semisolid agent to deliver drug substance at the site of vasospasm. Because the transient receptor potential protein blocker gel, transient receptor potential protein blocker slow-release solid or transient receptor potential protein blocker semisolid agent is delivered locally to the site, the dosage required to prevent vasospasm will be appropriate, and may reduce, prevent or circumvent the main side effect that prevents the administration of higher systemic doses, e.g., hypotension.

In another embodiment, the method comprises the step of surgically implanting or injecting an endothelin antagonist gel, endothelin antagonist slow-release solid or endothelin antagonist semisolid agent to deliver drug substance at the site of vasospasm. Because the endothelin antagonist gel, endothelin antagonist slow-release solid or endothelin antagonist semisolid agent is delivered locally to the site, the dosage required to prevent vasospasm will be appropriate, and may reduce, prevent or circumvent the main side effect that prevents the administration of higher systemic doses, e.g., hypotension.

In one embodiment, the method comprises the step of surgically implanting or injecting a gel, slow-release solid or semisolid agent in close proximity to targeted cerebral arteries. As desired or necessary, the gel, slow-release solid or semisolid agent may be positioned close to the cerebral arteries to produce the desired localized pharmacological effect. In one such embodiment, the distribution of gel, slow-release solid or semisolid agent may be tailored to anterior communicating artery aneurysms. In another some such embodiment, the distribution of gel, slow-release solid or semisolid agent may be tailored to middle cerebral artery aneurysms. In another some such embodiment, the distribution of gel, slow-release solid or semisolid agent may be tailored to internal carotid artery aneurysms. In another some such embodiment, the distribution of the gel, slow-release solid or semisolid agent may be tailored to an aneurysm located elsewhere in the subarachnoid space. In some such embodiments, the gel is a calcium channel blocker gel. In some such embodiments, the gel is a calcium channel antagonist gel. In some such embodiments, the gel is a calcium channel blocker gel. In some such embodiments, the gel is a calcium channel inhibitor gel. In some such embodiments, the gel is a transient receptor potential protein blocker gel. In some such embodiments, the gel is a endothelin antagonist gel. In some such embodiments, the slow-release solid agent is a calcium channel blocker slow-release solid agent. In some such embodiments, the slow-release solid agent is a calcium channel antagonist slow-release solid agent. In some such embodiments, the slow-release solid agent is a calcium channel blocker slow-release solid agent. In some such embodiments, the slow-release solid agent is a calcium channel inhibitor slow-release solid agent. In some such embodiments, the slow-release solid agent is a transient receptor potential protein blocker slow-release solid agent. In some such embodiments, the slow-release solid agent is a endothelin antagonist slow-release solid agent. In some such embodiments, the semisolid agent is a calcium channel blocker semisolid agent. In some such embodiments, the semisolid agent is a calcium channel antagonist semisolid agent. In some such embodiments, the semisolid agent is a calcium channel blocker semisolid agent. In some such embodiments, the semisolid agent is a calcium channel inhibitor semisolid agent. In some such embodiments, the semisolid agent is a transient receptor potential protein blocker semisolid agent. In some such embodiments, the semisolid agent is a endothelin antagonist semisolid agent.

In another embodiment, the present invention provides a method of treating cerebral vasospasm comprising providing a therapeutically effective amount of a calcium channel blocker, calcium channel antagonist, calcium channel inhibitor, endothelin receptor antagonist, or transient receptor potential protein blocker; and administering the therapeutically effective amount of the calcium channel blocker, calcium channel antagonist, calcium channel inhibitor, endothelin receptor antagonist, or transient receptor potential protein blocker in the subarachnoid space to a predetermined location in close proximity to a cerebral artery. In another embodiment, the therapeutic agent is subcutaneously administered to a predetermined location in close proximity to a cerebral artery. In another embodiment, the cerebral artery comprises an internal carotid, anterior cerebral, anterior communicating, posterior communicating, middle cerebral, posterior cerebral, basilar or vertebral artery.

Figures 2A, 2B, 2C:
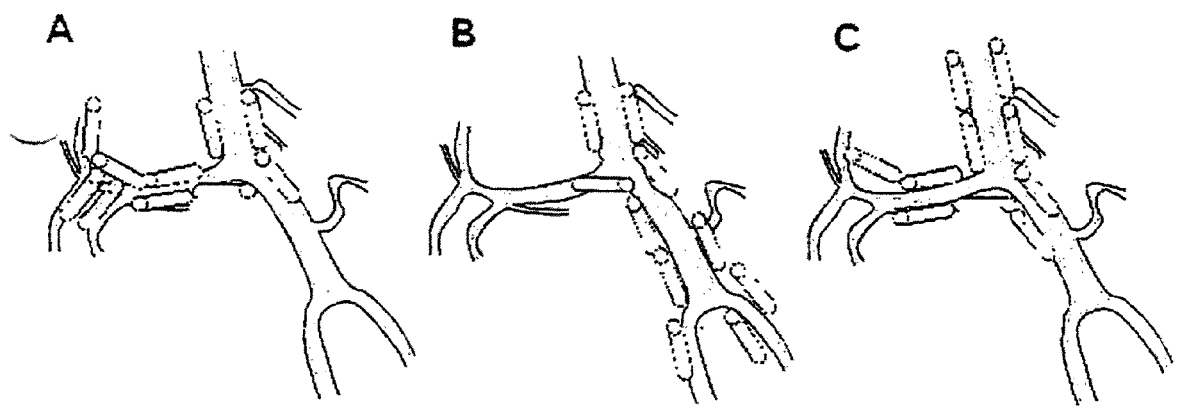
FIG. 2A shows an exemplary view of the application of calcium channel blocker, endothelin receptor antagonist, or putative transient receptor potential protein blocker gel, slow-release solid or semisolid compound to the anterior communicating artery according to one embodiment of the present invention.
FIG. 2B shows a view of one embodiment of the application of calcium channel blocker, endothelin receptor antagonist, or putative transient receptor potential protein blocker gel, slow-release solid or semisolid compound to the middle cerebral artery.
FIG. 2C shows a view of one embodiment of the application of calcium channel blocker, endothelin antagonist, or putative transient receptor potential protein blocker gel, slow-release solid or semisolid compound to the internal carotid artery.

In one embodiment, the method comprises the step of surgically implanting or injecting, as shown in FIG. 2A-C, nicardipine gel, nicardipine slow-release solid or nicardipine semisolid agent in close proximity to targeted cerebral arteries. As desired or necessary, the nicardipine gel, nicardipine slow-release solid or nicardipine semisolid agent may be positioned close to the cerebral arteries to produce the desired localized pharmacologic effect. In one such embodiment, referring to FIG. 2A, the distribution of nicardipine gel, nicardipine slow-release solid or nicardipine semisolid agent may be tailored to anterior communicating artery aneurysms. In another some such embodiment, referring to FIG. 2B, the distribution of nicardipine gel, nicardipine slow-release solid or nicardipine semisolid agent may be tailored to middle cerebral artery aneurysms. In another some such embodiment, referring to FIG. 2C, the distribution of nicardipine gel, nicardipine slow-release solid or nicardipine semisolid agent implants may be tailored to internal carotid artery aneurysms. In another some such embodiment, the distribution of the nicardipine gel, nicardipine slow-release solid or nicardipine semisolid agent may be tailored to an aneurysm located elsewhere in the subarachnoid space.

In another embodiment, the method comprises the step of surgically implanting or injecting, as shown in FIG. 2A-C, clevidipine gel, clevidipine slow-release solid or clevidipine semisolid agent implants in close proximity to targeted cerebral arteries. As desired or necessary, the clevidipine gel, clevidipine slow-release solid or clevidipine semisolid agent may be positioned close to the cerebral arteries to produce the desired localized pharmacologic effect. In one such embodiment, referring to FIG. 2A, the distribution of clevidipine gel, clevidipine slow-release solid or clevidipine semisolid agent implants may be tailored to anterior communicating artery aneurysms. In another some such embodiment, the distribution of clevidipine gel, clevidipine slow-release solid or clevidipine semisolid agent implants may be tailored to middle cerebral artery aneurysms. In another some such embodiment, referring to FIG. 2C, the distribution of clevidipine gel, clevidipine slow-release solid, or clevidipine semisolid agent implants may be tailored to internal carotid artery aneurysms.

In another some such embodiment, the distribution of the clevidipine gel, clevidipine slow-release solid or clevidipine semisolid agent may be tailored to an aneurysm located elsewhere in the subarachnoid space.

In another embodiment, the method comprises the step of surgically implanting or injecting nimodipine gel, nimodipine slow-release solid or nimodipine semisolid agent implants in close proximity to targeted cerebral arteries. As desired or necessary, the nimodipine gel, nimodipine slow-release solid or nimodipine semisolid agent may be positioned close to the cerebral arteries to produce the desired localized pharmacologic effect. In one such embodiment the distribution of nimodipine gel, nimodipine slow-release solid or nimodipine semisolid agent implants may be tailored to anterior communicating artery aneurysms. In another some such embodiment, the distribution of nimodipine gel, nimodipine slow-release solid or nimodipine semisolid agent implants may be tailored to middle cerebral artery aneurysms. In another some such embodiment the distribution of nimodipine gel, nimodipine slow-release solid, or nimodipine semisolid agent implants may be tailored to internal carotid artery aneurysms. In another some such embodiment, the distribution of the nimodipine gel, nimodipine slow-release solid or nimodipine semisolid agent may be tailored to an aneurysm located elsewhere in the subarachnoid space.

In another embodiment, the method comprises the step of surgically implanting or injecting, as shown in FIG. 2A-C, transient receptor potential protein blocker gel, transient receptor potential protein blocker slow-release solid or transient receptor potential protein blocker semisolid agent implants in close proximity to targeted cerebral arteries. As desired or necessary, the transient receptor potential protein blocker gel, transient receptor potential protein blocker slow-release solid or transient receptor potential protein blocker semisolid agent may be positioned close to the cerebral arteries to produce the desired localized pharmacologic effect. In one such embodiment, referring to FIG. 2A, the distribution of transient receptor potential protein blocker gel, transient receptor potential protein blocker slow-release solid or transient receptor potential protein blocker semisolid agent implants may be tailored to anterior communicating artery aneurysms. In another some such embodiment, the distribution of transient receptor potential protein blocker gel, transient receptor potential protein blocker slow-release solid or transient receptor potential protein blocker semisolid agent implants may be tailored to middle cerebral artery aneurysms. In another some such embodiment, referring to FIG. 2C, the distribution of transient receptor potential protein blocker gel, transient receptor potential protein blocker slow-release solid, or transient receptor potential protein blocker semisolid agent implants may be tailored to internal carotid artery aneurysms. In another some such embodiment, the distribution of the transient receptor potential protein blocker gel, transient receptor potential protein blocker slow-release solid or transient receptor potential protein blocker semisolid agent may be tailored to an aneurysm located elsewhere in the subarachnoid space.

In another embodiment, the method comprises the step of surgically implanting or injecting, as shown in FIG. 2A-C, endothelin antagonist gel, endothelin antagonist slow-release solid or endothelin antagonist semisolid agent implants in close proximity to targeted cerebral arteries. As desired or necessary, the endothelin antagonist gel, endothelin antagonist slow-release solid or endothelin antagonist semisolid agent may be positioned close to the cerebral arteries to produce the desired localized pharmacologic effect. In one such embodiment, referring to FIG. 2A, the distribution of endothelin antagonist gel, endothelin antagonist slow-release solid or endothelin antagonist semisolid agent implants may be tailored to anterior communicating artery aneurysms. In another some such embodiment, the distribution of endothelin antagonist gel, endothelin antagonist slow-release solid or endothelin antagonist semisolid agent implants may be tailored to middle cerebral artery aneurysms. In another some such embodiment, referring to FIG. 2C, the distribution of endothelin antagonist gel, endothelin antagonist slow-release solid, or endothelin antagonist semisolid compound implants may be tailored to internal carotid artery aneurysms. In another some such embodiment, the distribution of the endothelin antagonist gel, endothelin antagonist slow-release solid or endothelin antagonist semisolid agent may be tailored to an aneurysm located elsewhere in the subarachnoid space.

In another aspect, the present invention includes a method, the method comprising the step of administering a therapeutically effective amount of a calcium channel blocker subdurally, subarachnoidally, or subpially to a predetermined location in close proximity to at least one cerebral artery. It is desired that the therapeutically effective amount of the calcium channel blocker is implanted subdurally, subarachnoidally, or subpially and/or placed in close proximity to a cerebral artery or arteries.

Compositions

The compositions are delivered in therapeutically effective amounts. The term "effective amount" refers to the amount necessary or sufficient to realize a desired biologic effect. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. The effective amount for any particular application may vary depending on such factors as the disease or condition being treated, the particular calcium channel inhibitor, calcium channel antagonist, calcium channel blocker, transient receptor potential protein blocker, or endothelin antagonist being administered, the size of the subject, or the severity of the disease or condition. One of ordinary skill in the art may determine empirically the effective amount of a particular inhibitor and/or other therapeutic agent without necessitating undue experimentation. It is preferred generally that a maximum dose be used, that is, the highest safe dose according to some medical judgment. "Dose" and "dosage" are used. interchangeably herein.

For any compound described herein the therapeutically effective amount may be initially determined from preliminary in vitro studies and/or animal models. A therapeutically effective dose may also be determined from human data for calcium channel inhibitors, calcium channel antagonists, calcium channel blockers, transient receptor potential protein blockers, or endothelin antagonists which have been tested in humans and for compounds which are known to exhibit similar pharmacological activities, such as other related active agents. The applied dose may be adjusted based on the relative bioavailability and potency of the administered compound. Adjusting the dose to achieve maximal efficacy based on the methods described above and other methods as are well-known in the art is well within the capabilities of the ordinarily skilled artisan.

The formulations of calcium channel inhibitors, calcium channel antagonists, calcium channel blockers, transient receptor potential protein blockers, or endothelin antagonists may be administered in pharmaceutically acceptable solutions, which may routinely contain pharmaceutically acceptable concentrations of salt, buffering agents, preservatives, compatible carriers, adjuvants, and optionally other therapeutic ingredients.

For use in therapy, an effective amount of the calcium channel inhibitor, calcium channel antagonist, calcium channel blocker, transient receptor potential protein blocker, or endothelin antagonist may be administered to a subject by any mode that delivers the inhibitor to the desired surface. Administering the pharmaceutical composition may be accomplished by any means known to the skilled artisan. Routes of administration include, but are not limited to, intrathecal, intra-arterial, parenteral (e.g. intravenous), or intramuscular. The inhibitors and other therapeutics may be delivered to a subject during surgery to treat an underlying condition or side effect such as subarachnoid hemorrhage or peripheral vasospasm or during intra-arterial procedures.

The calcium channel inhibitor, calcium channel antagonist, channel blocker, transient receptor potential protein blocker, or endothelin antagonist, when it is desirable to deliver them locally, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active compounds may be in powder form for constitution with a suitable vehicle, e.g., sterile pyrogen-free water, before use.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

The calcium channel inhibitor, calcium channel blocker, and/or calcium channel antagonist, and optionally other therapeutics may be administered per se (neat) or in the form of a pharmaceutically acceptable salt. Other therapeutics may include, but are not limited to, a transient receptor potential protein blocker and endothelin antagonist. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley V C H, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts may be also obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The formulations may be presented conveniently in unit dosage form and may be prepared by any of the methods well known in the art of pharmacy. All methods include the step of bringing into association a calcium channel inhibitor, a calcium channel blocker, a calcium channel antagonist, endothelin antagonist, and/or transient receptor potential protein blocker, or a pharmaceutically acceptable salt or solvate thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, solvate or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly (orthoesters) and poly(anhydrides). Depot injectable formulations are also prepared by entrapping the drug in liposomes or microemulsions which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono-or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Another method of formulation of the compositions described herein involves conjugating the compounds described herein to a polymer that enhances aqueous solubility. Examples of suitable polymers include but are not limited to polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used. The polymer is conjugated via an ester linkage to one or more hydroxyls of an inventive epothilone using a protocol as essentially described by U.S.

Pat. No. 5,977,163 which is incorporated herein by reference. Particular conjugation sites include the hydroxyl off carbon-21 in the case of 21-hydroxy-derivatives of the present invention. Other conjugation sites include, but are not limited, to the hydroxyl off carbon 3 and/or the hydroxyl off carbon 7.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions described within the present invention contain a therapeutically effective amount of a calcium channel inhibitor, a calcium channel antagonist, a calcium channel blocker, an endothelin antagonist, and/or a transient receptor potential protein blocker and optionally other therapeutic agents included in a pharmaceutically-acceptable carrier. The term "pharmaceutically-acceptable carrier" as used herein refers to one or more compatible solid or liquid filler, diluents or encapsulating substances which are suitable for administration to a human or other vertebrate animal. The term "carrier" as used herein refers to an organic or inorganic ingredient, natural or synthetic, with which the active ingredient is combined to facilitate the application. The components of the pharmaceutical compositions also are capable of being commingled in a manner such that there is no interaction which would substantially impair the desired pharmaceutical efficiency.

The therapeutic agent(s), including the calcium channel inhibitor, the calcium channel antagonist, the calcium channel blocker, a transient receptor potential protein blocker, and/or an endothelin antagonist may be provided in particles. The term "particles" as used herein refers to nano or microparticles (or in some instances larger) that may contain in whole or in part the calcium channel inhibitor, calcium channel antagonist, or calcium channel blocker or the other therapeutic agent(s) as described herein, including, but not limited to, endothelin antagonist and transient receptor potential protein blocker. The particles may contain the therapeutic agent(s) in a core surrounded by a coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, etc., and any combination thereof. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules that contain the calcium channel inhibitor, calcium channel antagonist, and/or calcium channel blocker in a solution or in a semi-solid state. The particles may be of virtually any shape.

Both non-biodegradable and biodegradable polymeric materials may be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels as described by Sawhney et al in Macromolecules (1993) 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. In order to prolong the effect of a drug, it often is desirable to slow the absorption of the drug from subcutaneous, intrathecal, or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. The term "controlled release" is intended to refer to any drug-containing formulation in which the manner and profile of drug release from the formulation are controlled. This refers to immediate as well as non-immediate release formulations, with non-immediate release formulations including, but not limited to, sustained release and delayed release formulations. The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug form is accomplished by dissolving or suspending the drug in an oil vehicle. The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. The term "long-term" release, as used herein, means that the implant is constructed and arranged to deliver therapeutic levels of the active ingredient for at least 7 days, and preferably about 30 to about 60 days. Long-term sustained release implants are well-known to those of ordinary skill in the art and include some of the release systems described above.

Delivery Systems

The present invention provides a semisolid delivery system for therapeutic agents and combination semisolid, multiparticulate, therapeutic delivery system for therapeutic agents. In one aspect, the present invention comprises of a delivery system that utilizes a semisolid, biodegradable, biocompatible delivery system or a biodegradable, biocompatible multiparticulate dispersed and suspended in a semisolid, biodegradable, biocompatible biodegradable delivery system for injection, deposition or implantation within or upon the body so as to facilitate local therapeutic effects. The term "biodegradable" as used herein refers to material that will degrade actively or passively over time by simple chemical processes, by action of body enzymes or by other similar mechanisms in the human body. The term "biocompatible" as used herein refers to causing no clinically relevant tissue irritation or necrosis at local site necessitating removal of the device prior to end of therapy based on a clinical risk/benefit assessment. The terms "in the body", "void volume", "resection pocket", "excavation", "injection site", "deposition site" or "implant site" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof. In one embodiment, the therapeutic agent is calcium channel inhibitor, the calcium channel antagonist, the calcium channel blocker, a transient receptor potential protein blocker, and/or an endothelin antagonist or pharmaceutically acceptable salts thereof.

In one aspect, the semisolid delivery system comprises partially or in whole a biocompatible, biodegradable, viscous semisolid wherein the semisolid comprises a hydrogel. The term "hydrogel" as used herein refers to a substance resulting in a solid, semisolid, pseudoplastic, or plastic structure containing a necessary aqueous component to produce a gelatinous or jelly-like mass. The hydrogel incorporates and retains significant amounts of $H_2O$, which eventually will reach an equilibrium content in the presence of an aqueous environment. In one embodiment, glyceryl monooleate, hereinafter referred to as GMO, is the intended semisolid delivery system or hydrogel. However, many hydrogels, polymers, hydrocarbon compositions and fatty acid derivatives having similar physical/chemical properties with respect to viscosity/rigidity may function as a semisolid delivery system.

In one embodiment, the gel system is produced by heating GMO above its melting point (40-50° C.) and by adding a warm aqueous-based buffer or electrolyte solution, such as, for example, phosphate buffer or normal saline, which thus produces a three-dimensional structure. The aqueous-based buffer may be comprised of other aqueous solutions or combinations containing semi-polar solvents.

GMO provides a predominantly lipid-based hydrogel, which has the ability to incorporate lipophilic materials. The term "lipophilic" as used herein refers to preferring or possessing an affinity for a non-polar environment compared to a polar or aqueous environment. GMO further provides internal aqueous channels that incorporate and deliver hydrophilic compounds. The term "hydrophilic" as used herein refers to a material or substance having an affinity for polar substances, such as water. It is recognized that at room temperature (~25° C.), the gel system may exhibit differing phases which comprise a broad range of viscosity measures.

In one embodiment, two gel system phases are utilized due to their properties at room temperature and physiologic temperature (about 37° C.) and pH (about 7.4). Within the two gel system phases, the first phase is a lamellar phase of approximately 5% to approximately 15% $H_2O$ content and approximately 95% to approximately 85% GMO content. The lamellar phase is a moderately viscous fluid, that may be easily manipulated, poured and injected. The second phase is a cubic phase consisting of approximately 15% to approximately 40% $H_2O$ content and approximately 85%-60% GMO content. It has an equilibrium water content at approximately 35% to approximately 40% by weight. The term "equilibrium water content" as used herein refers to maximum water content in the presence of excess water. Thus the cubic phase incorporates water at approximately 35 to approximately 40% by weight. The cubic phase is highly viscous. Viscosity may be measured, for example, via a Brookfield viscometer. The viscosity exceeds 1.2 million centipoise (cp); wherein 1.2 million cp being the maximum measure of viscosity obtainable via the cup and bob configuration of the Brookfield viscometer. In some such embodiments, a therapeutic agent may be incorporated into the semisolid so as to provide a system for sustained, continuous delivery thereof. In some such embodiments, the therapeutic agent is nicardipine. In some such embodiments, the therapeutic agent is nimodipine. In some such embodiments, the therapeutic agent is clevidipine. In some such embodiments, the therapeutic agent is nicardipine. In some such embodiments, the therapeutic agent is clazosentan. In some such embodiments, the therapeutic agent is atrasentan. In some such embodiments, the therapeutic agent is SKF 96365. In some such embodiments, the therapeutic agent is LOE 908. In some such embodiments, the therapeutic agent is a calcium channel blocker. In some such embodiments, the therapeutic agent is a calcium channel antagonist. In some such embodiments, the therapeutic agent is a calcium channel inhibitor. In some such embodiments, the therapeutic agent is an endothelin antagonist. In some such embodiments, the therapeutic agent is a transient receptor potential protein blocker. In some such embodiments, other therapeutic agents, biologically-active agents, drugs, medicaments and inactives may be incorporated into the semisolid for providing a local biological, physiological, or therapeutic effect in the body at various release rates.

In some embodiments, alternative semisolids, modified formulations and methods of production are utilized such that the lipophilic nature of the semisolid is altered, or in the alternative, the aqueous channels contained within the semisolid are altered. Thus, various therapeutic agents in varying concentrations may diffuse from the semisolid at differing rates, or be released therefrom over time via the aqueous channels of the semisolid. Hydrophilic substances may be utilized to alter semisolid consistency or therapeutic agent release by alteration of viscosity, fluidity, surface tension or the polarity of the aqueous component. For example, glyceryl monostearate (GMS), which is structurally identical to GMO with the exception of a double bond at Carbon 9 and Carbon 10 of the fatty acid moiety rather than a single bond, does not gel upon heating and the addition of an aqueous component, as does GMO. However, because GMS is a surfactant, GMS is miscible in $H_2O$ up to approximately 20% weight/weight. The term "surfactant" as used herein refers to a surface active agent, thus being miscible in $H_2O$ in limited concentrations as well as polar substances. Upon heating and stirring, the 80% $H_2O$/20% GMS combination produces a spreadable paste having a consistency resembling hand lotion. The paste then is combined with melted GMO so as to form the cubic phase gel possessing a high viscosity as stated heretofore. In some such embodiments, the therapeutic agent is nicardipine. In some such embodiments, the therapeutic agent is nimodipine. In some such embodiments, the therapeutic agent is clazosentan. In some such embodiments, the therapeutic agent is SKF 96365. In some such embodiments, the therapeutic agent is LOE 908. In some such embodiments, the therapeutic agent is clevidipine. In some such embodiments, the therapeutic agent is a calcium channel inhibitor. In some such embodiments, the therapeutic agent is a calcium channel antagonist. In some such embodiments, the therapeutic agent is a calcium channel blocker. In some such embodiments, the therapeutic agent is a transient receptor potential protein blocker. In some such embodiments, the therapeutic agent is an endothelin antagonist. In some such embodiments, the therapeutic agent is nicardipine, nimodipine, clevidipine, transient receptor potential protein blocker, or pharmaceutically acceptable salts thereof.

In another embodiment, hydrolyzed gelatin, such as commercially available Gelfoam™, is utilized for altering the aqueous component. Approximately 6.25% to 12.50% concentration of Gelfoam™ by weight may be placed in approximately 93.75% to 87.50% concentration of $H_2O$ respectively by weight or other aqueous based buffer. Upon heating and stirring, the $H_2O$ (or other aqeuous buffer)/Gelfoam™ combination produces a thick gelatinous substance. The resulting substance is combined with GMO, whereby a product so formed swells and forms a highly viscous, translucent gel being less malleable in comparison to neat GMO gel alone.

In another embodiment, polyethylene glycols (PEG's) may be utilized for altering the aqueous component to aid in drug solubilization. Approximately 0.5% to 40% concentration of PEG's (depending on PEG molecular weight) by weight placed in approximately 99.5% to 60% concentration of $H_2O$ respectively by weight or other aqueous based buffer. Upon heating and stirring, the $H_2O$ (or other aqeuous buffer)/PEG combination produces a viscous liquid to a semisolid substance. The resulting substance is combined with GMO, whereby a product so formed swells and forms a highly viscous gel.

Without being limited by theory, it is postulated the therapeutic agent releases from the semisolid through diffusion, conceivably in a biphasic manner. A first phase involves, for example, a lipophilic drug contained within the lipophilic membrane diffuses therefrom into the aqueous channel. The second phase involves diffusion of the drug from the aqueous channel into the external environment. Being lipophilic, the drug may orient itself inside the GMO gel within its proposed lipid bi-layer structure. Thus, incorporating greater than approximately 7.5% of the drug, for example BCNU, by weight into GMO causes a loss of the integrity of the three-dimensional structure whereby the gel system no longer maintains the semisolid cubic phase, and reverts to the viscous lamellar phase liquid. In some such embodiments, the therapeutic agent is nicardipine. In some such embodiments, the therapeutic agent is nimodipine. In some such embodiments, the therapeutic agent is clevidipine. In some such embodiments, the therapeutic agent is a calcium channel inhibitor. In some such embodiments, the therapeutic agent is a calcium channel antagonist. In some such embodiments, the therapeutic agent is a calcium channel blocker. In some such embodiments, the therapeutic agent is a transient receptor potential protein blocker. In some such embodiments, the therapeutic agent is an endothelin antagonist. In some such embodiments, the therapeutic agent is nicardipine, nimodipine, clevidipine, transient receptor potential protein blocker, or pharmaceutically acceptable salts thereof. In another embodiment, about 1 to about 45% of therapeutic agent is incorporated by weight into a GMO gel at physiologic temperature without disruption of the normal three-dimensional structure. As a result, this system allows the ability of significantly increased flexibility with drug dosages. Because the delivery system is malleable, it may be delivered and manipulated in an implant site, for example, adjacent to cerebral arteries or the subarachnoid space, so as to adhere and conform to contours of walls, spaces, or other voids in the body as well as completely fill all voids existing. The delivery system ensures drug distribution and uniform drug delivery throughout the implant site. Ease of delivery and manipulation of the delivery system within a space, for example, but not limited to the subarachnoid space, is facilitated via a semisolid delivery apparatus. A semisolid delivery apparatus facilitates targeted and controlled delivery of the delivery system.

In one embodiment, the multiparticulate component is comprised of biocompatible, biodegradable, polymeric or non-polymeric systems utilized to produce solid structures including but not limited to nonpareils, pellets, crystals, agglomerates, microspheres, or nanoparticles.

In another embodiment, the multiparticulate component comprises of poly(lactic-co-glycolide) (PLGA's). PLGA's are biodegradable polymer materials used for controlled and extended therapeutic agent delivery within the body. Such delivery systems offer enhanced therapeutic efficacy and reduced overall toxicity as compared to frequent periodic, systemic dosing. Without being limited by theory, it is postulated that PLGA's systems consisting of differing molar ratios of the monomeric subunits will facilitate greater flexibility in engineering precise release profiles for accommodating targeted therapeutic agent delivery through alterations in the rate of polymer degradation. In one embodiment, the PLGA composition is sufficiently pure so as to be biocompatible and remains biocompatible upon biodegradation. In one embodiment, the PLGA polymer is designed and configured into microspheres having a therapeutic agent or drug entrapped therein, whereby the therapeutic agent is subsequently released therefrom by a method to be described in greater detail below. In some such embodiments, the therapeutic agent is nicardipine. In some such embodiments, the therapeutic agent is nimodipine. In some such embodiments, the therapeutic agent is clevidipine. In some such embodiments, the therapeutic agent is a calcium channel inhibitor. In some such embodiments, the therapeutic agent is a calcium channel antagonist. In some such embodiments, the therapeutic agent is a calcium channel blocker. In some such embodiments, the therapeutic agent is a transient receptor potential protein blocker. In some such embodiments, the therapeutic agent is an endothelin antagonist. In some such embodiments, the therapeutic agent is nicardipine, nimodipine, clevidipine, transient receptor potential protein blocker, or pharmaceutically acceptable salts thereof.

In another embodiment, the multiparticulate component is comprised of poly d,l(lactic-co-caprolactone). This provides a biodegradable polymer material used for controlled and extended therapeutic agent delivery within the body with a similar drug release mechanism to that of the PLGA polymers. In one embodiment, the multiparticulate microspheres also are produced using biodegradable and/or biocompatible non-polymeric materials such as GMS.

In another embodiment, the multiparticulate component is further modified by methods used to encapsulate or coat the multiparticulate components using polymers of the same composition with the same or different drug substances, different polymers with the same or different drug substances, or with multiple layering processes containing no drug, the same drug, a different drug, or multiple drug substances. This allows the production of a multi-layered (encapsulated) multiparticulate system with a wide range of drug release profiles for single or multiple drug agents simultaneously. In another embodiment, coating materials which control the rate of physical drug diffusion from the multiparticulate may be utilized alone or in concert with the aforementioned preferred embodiments and envisioned embodiments.

In another aspect, the present invention provides a delivery system that utilizes PLGA. The PLGA polymer contains ester bonds, which are labile to hydrolysis. The term "labile" as used herein refers to subject to increased degradation. When $H_2O$ penetrates the PLGA polymer, the ester bonds thereof are hydrolyzed, and monomers, being water soluble, are removed from the PLGA polymer, thus facilitating the physical release of the entrapped drug over time. In some such embodiments, other classes of synthetic biodegradable, biocompatible polymers may be used for controlled and extended therapeutic agent delivery within the body, including polyanhydrides, poly(phosphates), polydioxanone, cellulosics and acrylics which are extended as non-limiting examples. In some such embodiments, nonpolymeric materials may be utilized for controlled and extended therapeutic agent delivery within the body, including but not limited to sterols, sucrose fatty acid esters, fatty acids, and cholesteryl esters, which are extended as non-limiting examples.

In another aspect, the present invention provides a semi-solid delivery system, which acts as a vehicle for local delivery of therapeutic agents, comprising a lipophilic, hydrophilic or amphophilic, solid or semisolid substance, heated above its melting point and thereafter followed by inclusion of a warm aqueous component so as to produce a gelatinous composition of variable viscosity based on water content. The therapeutic agent(s) is incorporated and dispersed into the melted lipophilic component or the aqueous buffer component prior to mixing and formation of the semisolid system. The gelatinous composition is placed within the semisolid delivery apparatus for subsequent placement, or deposition. Being malleable, the gel system is easily delivered and manipulated via the semisolid delivery apparatus in an implant site, where it adheres and conforms to contours of the implantation site, spaces, or other voids in the body as well as completely filling all voids existing. Alternatively, a multiparticulate component, comprised of a biocompatible polymeric or non-polymeric system, is utilized for producing microspheres having a therapeutic agent entrapped therein. Following final processing methods, the microspheres are incorporated into the semisolid system and subsequently placed within the semisolid delivery apparatus so as to be easily delivered therefrom into an implant site or comparable space, whereby the therapeutic agent is subsequently released therefrom by (a) drug release mechanism(s).

Identification of Calcium Channel Inhibitors, Calcium Channel Antagonists, and Calcium Channel Blockers Other activity inhibitors, blockers or antagonists may be identified by those of skill in the art following the guidance described herein.

Libraries of agents or other putative agents may be screened to identify new useful calcium channel activity inhibitors, calcium channel activity antagonists, or calcium channel activity blockers. Putative compounds may be synthesized from peptides or other biomolecules including but not limited to saccharides, fatty acids, sterols, isoprenoids, purines, pyrimidines, derivatives or structural analogs of the above, or combinations thereof and the like. Phage display libraries and chemical combinatorial libraries may be used to develop and select synthetic compounds capable of inhibiting, antagonizing, and/or blocking calcium channels. Also envisioned in the invention is the use of compounds made from peptoids, random bio-oligomers (U.S. Pat. No. 5,650,489), benzodiazepines, diversomeres such as dydantoins, benzodiazepines and dipeptides, nonpeptidal peptidomimetics with a beta-D-glucose scaffolding, oligocarbamates or peptidyl phosphonates.

Library technology may be used to identify small molecules, including small peptides, which bind to a calcium channel ligand binding site, or a protein interaction domain of a calcium channel. One advantage of using libraries for antagonist identification is the facile manipulation of millions of different putative candidates of small size in small reaction volumes (i.e., in synthesis and screening reactions). Another advantage of libraries is the ability to synthesize calcium channel inhibitors, calcium channel antagonists, and/or calcium channel blockers that might not otherwise be attainable using naturally occurring sources, particularly in the case of non-peptide moieties.

Many if not all of these agents maybe synthesized using recombinant or chemical libraries. A vast array of candidate compounds maybe generated from libraries of synthetic or natural compounds. Libraries of natural compounds in the form of bacterial, fungal, plant and animal extracts are available or may readily produced. Natural and synthetically produced libraries and compounds maybe readily modified through conventional chemical, physical, and biochemical means. In addition, compounds known to bind to and thereby act as antagonists, inhibitors, or blockers of calcium channels may be subjected to directed or random chemical modifications such as acylation, alkylation, esterification, amidification, etc. to produce structural analogs that may function similarly or perhaps with greater specificity.

Small molecule combinatorial libraries also may be generated. A combinatorial library of small organic compounds is a collection of closely related analogs that differ from each other in one or more points of diversity and are synthesized by organic techniques using multi-step processes. As an example, analogs of gadolinium chloride or lanthanum chloride may be generated that function as calcium channel inhibitors, calcium channel blockers or calcium channel antagonists but that do not inhibit, antagonize, or block other channels. Analogs of these compounds maybe synthesized using combinatorial libraries.

Combinatorial libraries include a vast number of small organic compounds. One type of combinatorial library is prepared by means of parallel synthesis methods to produce a compound array. The term "compound array" as used herein refers to a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

The compounds generated using the recombinant and chemical libraries described herein may be screened initially to identify putative agents by virtue of their ability to bind to a calcium channel. Compounds such as library members may be screened for their ability to bind to a calcium channel in vitro using standard binding assays well known to the ordinary artisan and described below. For binding to a calcium channel, the calcium channel may be presented in a number of ways, including, but not limited to, cells expressing the calcium channel of interest, an isolated extracellular domain of a calcium channel, a fragment thereof, or a fusion protein of the extracellular domain of a calcium channel, and another protein such as an immunoglobulin or a GST polypeptide or in a purified (e.g., a recombinantly produced) form. For some high throughput screening assays, the use of purified forms of a calcium channel, its extracellular domain or a fusion of its extracellular domain with another protein may be preferable. Isolation of binding partners may be performed in solution or in solid state according to well-known methods.

Standard binding assays are well known in the art, and a number of these are suitable in the present invention including ELISA, competition binding assay, sandwich assays, radioreceptor assays using radioactively labeled ligands or substrates of calcium channels (with the binding of the native, radioactively labeled, activator being competed with by the putative antagonist, inhibitor, or blocker), electrophoretic mobility shift assays, immunoassays, cell-based assays such as two-or three-hybrid screens, etc. The nature of the assay is not essential provided it is sufficiently sensitive to detect binding of a small number of library members.

A variety of other reagents also may be included in the binding mixture. These include reagents such as salts, buffers, neutral proteins (e.g., albumin), detergents, etc. which may be used to facilitate optimal molecular interactions. Such a reagent also may reduce non-specific or background interactions of the reaction components. Other reagents that improve the efficiency of the assay also may be used. The mixture of the foregoing assay materials is incubated under conditions under which the calcium channel normally specifically binds one or more of its activators. The order of addition of components, incubation temperature, time of incubation, and other parameters of the assay may be determined readily. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between the compounds is detected by any convenient method available to the user.

Typically, a plurality of assay mixtures are run in parallel with different agent concentrations to obtain a different response to the various concentrations. One of these concentrations serves as a negative control, i.e., at zero concentration of agent or at a concentration of agent below the limits of assay detection.

Once compounds have been identified that are capable of interacting with a calcium channel, these compounds may be screened further for their ability to modulate ion flux across these calcium channels.

Identification of Transient Receptor Potential Protein Blockers

Other activity inhibitors, blockers or antagonists of transient receptor potential proteins may be identified by those of skill in the art following the guidance described herein.

Libraries of agents or other putative agents may be screened to identify new useful transient receptor potential protein activity inhibitors, transient receptor potential activity antagonists, transient receptor potential protein activity blockers. Putative compounds may be synthesized from peptides or other biomolecules including but not limited to saccharides, fatty acids, sterols, isoprenoids, purines, pyrimidines, derivatives or structural analogs of the above, or combinations thereof and the like. Phage display libraries and chemical combinatorial libraries may be used to develop and select synthetic compounds capable of inhibiting, antagonizing, and/or transient receptor potential proteins. Also envisioned in the invention is the use of compounds made from peptoids, random bio-oligomers (U.S. Pat. No. 5,650,489), benzodiazepines, diversomeres such as dydantoins, benzodiazepines and dipeptides, nonpeptidal peptidomimetics with a beta-D-glucose scaffolding, oligocarbamates or peptidyl phosphonates.

Library technology may be used to identify small molecules, including small peptides, which bind to a transient receptor potential protein binding site, or a protein interaction domain of a transient receptor potential protein. One advantage of using libraries for antagonist identification is the facile manipulation of millions of different putative candidates of small size in small reaction volumes (i.e., in synthesis and screening reactions). Another advantage of libraries is the ability to synthesize transient receptor potential protein inhibitors, transient receptor potential protein antagonists, and/or transient receptor potential protein blockers that might not otherwise be attainable using naturally occurring sources, particularly in the case of non-peptide moieties.

Many if not all of these agents maybe synthesized using recombinant or chemical libraries. A vast array of candidate compounds maybe generated from libraries of synthetic or natural compounds. Libraries of natural compounds in the form of bacterial, fungal, plant and animal extracts are available or may readily produced. Natural and synthetically produced libraries and compounds maybe readily modified through conventional chemical, physical, and biochemical means. In addition, compounds known to bind to and thereby act as antagonists, inhibitors, or blockers of transient receptor potential proteins may be subjected to directed or random chemical modifications such as acylation, alkylation, esterification, amidification, etc. to produce structural analogs that may function similarly or perhaps with greater specificity.

Small molecule combinatorial libraries also may be generated. A combinatorial library of small organic compounds is a collection of closely related analogs that differ from each other in one or more points of diversity and are synthesized by organic techniques using multi-step processes. As an example, analogs of SKF 96365 or LOW 908 may be generated that function as transient receptor potential protein inhibitors, transient receptor potential protein blockers or transient receptor potential protein antagonists but that do not inhibit, antagonize, or block other channels. Analogs of these compounds maybe synthesized using combinatorial libraries.

Combinatorial libraries include a vast number of small organic compounds. One type of combinatorial library is prepared by means of parallel synthesis methods to produce a compound array. The term "compound array" as used herein refers to a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

The compounds generated using the recombinant and chemical libraries described herein may be screened initially to identify putative agents by virtue of their ability to bind to a calcium channel. Compounds such as library members may be screened for their ability to bind to a transient receptor potential protein in vitro using standard binding assays well known to the ordinary artisan and described below. For binding to a transient receptor potential protein, the transient receptor potential protein may be presented in a number of ways, including, but not limited to, cells expressing the transient receptor potential protein of interest, an isolated extracellular domain of a transient receptor potential protein, a fragment thereof, or a fusion protein of the extracellular domain of a transient receptor potential protein, and another protein such as an immunoglobulin or a GST polypeptide or in a purified (e.g., a recombinantly produced) form. For some high throughput screening assays, the use of purified forms of a transient receptor potential protein, its extracellular domain or a fusion of its extracellular domain with another protein may be preferable. Isolation of binding partners may be performed in solution or in solid state according to well-known methods.

Standard binding assays are well known in the art, and a number of these are suitable in the present invention including ELISA, competition binding assay, sandwich assays, radioreceptor assays using radioactively labeled ligands or substrates of transient receptor potential protein (with the binding of the native, radioactively labeled, activator being competed with by the putative antagonist, inhibitor, or blocker), electrophoretic mobility shift assays, immunoassays, cell-based assays such as two-or three-hybrid screens, etc. The nature of the assay is not essential provided it is sufficiently sensitive to detect binding of a small number of library members.

A variety of other reagents also may be included in the binding mixture. These include reagents such as salts, buffers, neutral proteins (e.g., albumin), detergents, etc. which may be used to facilitate optimal molecular interactions. Such a reagent also may reduce non-specific or background interactions of the reaction components. Other reagents that improve the efficiency of the assay also may be used. The mixture of the foregoing assay materials is incubated under conditions under which the transient receptor potential protein normally specifically binds one or more of its activators. The order of addition of components, incubation temperature, time of incubation, and other parameters of the assay may be determined readily. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between the compounds is detected by any convenient method available to the user.

Typically, a plurality of assay mixtures are run in parallel with different agent concentrations to obtain a different response to the various concentrations. One of these concentrations serves as a negative control, i.e., at zero concentration of agent or at a concentration of agent below the limits of assay detection.

Once compounds have been identified that are capable of interacting with a transient receptor potential protein, these compounds may be screened further for their ability to modulate activity across these transient receptor potential proteins.

Identification of Endothelin Receptor Antagonists

Other activity antagonists of endothelin receptors may be identified by those of skill in the art following the guidance described herein.

Libraries of agents or other putative agents may be screened to identify new useful endothelin receptor activity inhibitors, endothelin receptor activity antagonists, endothelin receptor activity blockers. Putative compounds may be synthesized from peptides or other biomolecules including but not limited to saccharides, fatty acids, sterols, isoprenoids, purines, pyrimidines, derivatives or structural analogs of the above, or combinations thereof and the like. Phage display libraries and chemical combinatorial libraries may be used to develop and select synthetic compounds capable of inhibiting, antagonizing, and/or blocking endothelin receptors. Also envisioned in the invention is the use of compounds made from peptoids, random bio-oligomers (U.S. Pat. No. 5,650,489), benzodiazepines, diversomeres such as dydantoins, benzodiazepines and dipeptides, nonpeptidal peptidomimetics with a beta-D-glucose scaffolding, oligocarbamates or peptidyl phosphonates.

Library technology may be used to identify small molecules, including small peptides, which bind to an endothelin receptor binding site, or a protein interaction domain of a endothelin receptor. One advantage of using libraries for antagonist identification is the facile manipulation of millions of different putative candidates of small size in small reaction volumes (i.e., in synthesis and screening reactions). Another advantage of libraries is the ability to synthesize endothelin receptor inhibitors, endothelin receptor antagonists, and/or endothelin receptor blockers that might not otherwise be attainable using naturally occurring sources, particularly in the case of non-peptide moieties.

Many if not all of these agents maybe synthesized using recombinant or chemical libraries. A vast array of candidate compounds maybe generated from libraries of synthetic or natural compounds. Libraries of natural compounds in the form of bacterial, fungal, plant and animal extracts are available or may readily produced. Natural and synthetically produced libraries and compounds maybe readily modified through conventional chemical, physical, and biochemical means. In addition, compounds known to bind to and thereby act as antagonists, inhibitors, or blockers of endothelin receptors may be subjected to directed or random chemical modifications such as acylation, alkylation, esterification, amidification, etc. to produce structural analogs that may function similarly or perhaps with greater specificity.

Small molecule combinatorial libraries also may be generated. A combinatorial library of small organic compounds is a collection of closely related analogs that differ from each other in one or more points of diversity and are synthesized by organic techniques using multi-step processes. As an example, analogs of clazosenten may be generated that function as endothelin receptor inhibitors, endothelin receptor blockers or endothelin receptor antagonists but that do not inhibit, antagonize, or block other channels. Analogs of these compounds maybe synthesized using combinatorial libraries.

Combinatorial libraries include a vast number of small organic compounds. One type of combinatorial library is prepared by means of parallel synthesis methods to produce a compound array. The term "compound array" as used herein refers to a collection of compounds identifiable by their spatial addresses in Cartesian coordinates and arranged such that each compound has a common molecular core and one or more variable structural diversity elements. The compounds in such a compound array are produced in parallel in separate reaction vessels, with each compound identified and tracked by its spatial address. Examples of parallel synthesis mixtures and parallel synthesis methods are provided in PCT published patent application WO95/18972, published Jul. 13, 1995 and U.S. Pat. No. 5,712,171 granted Jan. 27, 1998 and its corresponding PCT published patent application WO96/22529, which are hereby incorporated by reference.

The compounds generated using the recombinant and chemical libraries described herein may be screened initially to identify putative agents by virtue of their ability to bind to a endothelin receptor. Compounds such as library members may be screened for their ability to bind to an endothelin receptor in vitro using standard binding assays well known to the ordinary artisan and described below. For binding to a endothelin receptor, the endothelin receptor may be presented in a number of ways, including, but not limited to, cells expressing the endothelin receptor of interest, an isolated extracellular domain of an endothelin receptor, a fragment thereof, or a fusion protein of the extracellular domain of an endothelin receptor, and another protein such as an immunoglobulin or a GST polypeptide or in a purified (e.g., a recombinantly produced) form. For some high throughput screening assays, the use of purified forms of an endothelin receptor, its extracellular domain or a fusion of its extracellular domain with another protein may be preferable. Isolation of binding partners may be performed in solution or in solid state according to well-known methods.

Standard binding assays are well known in the art, and a number of these are suitable in the present invention including ELISA, competition binding assay, sandwich assays, radioreceptor assays using radioactively labeled ligands or substrates of an endothelin receptor (with the binding of the native, radioactively labeled, activator being competed with by the putative antagonist, inhibitor, or blocker), electrophoretic mobility shift assays, immunoassays, cell-based assays such as two-or three-hybrid screens, etc. The nature of the assay is not essential provided it is sufficiently sensitive to detect binding of a small number of library members.

A variety of other reagents also may be included in the binding mixture. These include reagents such as salts, buffers, neutral proteins (e.g., albumin), detergents, etc. which may be used to facilitate optimal molecular interactions. Such a reagent also may reduce non-specific or background interactions of the reaction components. Other reagents that improve the efficiency of the assay also may be used. The mixture of the foregoing assay materials is incubated under conditions under which the endothelin receptor normally specifically binds one or more of its activators. The order of addition of components, incubation temperature, time of incubation, and other parameters of the assay may be determined readily. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between the compounds is detected by any convenient method available to the user.

Typically, a plurality of assay mixtures are run in parallel with different agent concentrations to obtain a different response to the various concentrations. One of these concentrations serves as a negative control, i.e., at zero concentration of agent or at a concentration of agent below the limits of assay detection.

Once compounds have been identified that are capable of interacting with an endothelin receptor, these compounds may be screened further for their ability to modulate activity across these endothelin receptors.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein may also be used in the practice or testing of the present invention, the preferred methods and materials are now described. All publications mentioned herein are incorporated herein by reference to disclose and described the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The present invention may be embodied in other specific forms without departing from the spirit or essential attributes thereof and, accordingly, reference should be made to the appended claims, rather than to the foregoing specification, as indicating the scope of the invention.

The invention claimed is:

1. A method of treating a cerebral vasospasm in a human subject, the method comprising the steps:
    a) providing a flowable pharmaceutical composition for sustained release comprising a therapeutic amount of a therapeutic agent and a carrier, wherein the therapeutic agent comprises an L-type voltage-gated calcium channel inhibitor and the carrier comprises a plurality of microparticles, wherein the L-type voltage-gated calcium channel inhibitor is dispersed throughout each microparticle;
    b) administering the pharmaceutical composition to the human subject locally via surgical injection into the subarachnoicl space in a cistern closest to a cerebral artery at risk for vasospasm, such that the composition flows around the cerebral artery without entering the systemic circulation in an amount to cause unwanted side effects;
    wherein the pharmaceutical composition produces a localized pharmacologic effect: and
    wherein the therapeutic amount is effective to treat the cerebral vasospasm.

2. The method of claim 1, wherein the therapeutic agent comprises a calcium channel antagonist.

3. The method of claim 1, wherein the therapeutic agent comprises a transient receptor potential protein blocker.

4. The method of claim 1, wherein the therapeutic agent comprises an endothelin receptor antagonist.

5. The method of claim 1, wherein the carrier is a gel compound.

6. The method of claim 1, wherein the carrier is a semisolid compound.

7. The method of claim 1, wherein the carrier is a slow-release solid compound.

8. The method of claim 1, wherein the therapeutic agent is selected from the group consisting of amlodipine, aranidipine, azelnidipine, bamidipinc, benidipine, bepridil, cinaldipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, verapamil or a combination thereof.

9. The method of claim 1, wherein the therapeutic agent is selected from the group consisting of A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL2500, PD-161721, RES 701-1, and RO 468443.

10. The method of claim 1, wherein the therapeutic agent is selected from the group consisting of SKF 96365 and LOE 908.

11. The method of claim 1, wherein the cistern closest to a cerebral artery at risk for vasospasm in step (b) is from about 0.001 mm to about 10 mm from the cerebral artery.

12. A method of treating a human subject for vasospasm after subarachnoid hemorrhage in at least one cerebral artery, the method comprising the steps of:
  a) providing a flowable pharmaceutical composition for sustained release comprising a therapeutic amount of a therapeutic agent and a carrier, wherein the therapeutic agent comprises an L-type voltage-gated calcium channel inhibitor and the carrier comprises a plurality of microparticles, wherein the L-type voltage-gated calcium channel inhibitor is dispersed throughout each microparticle;
  b) administering the pharmaceutical composition to the human subject via surgical injection into the subarachnoid space in a cistern closest to a cerebral artery at risk for vasospasm, such that the composition flows around the cerebral artery without entering the systemic circulation in an amount to cause unwanted side effects;
    wherein the pharmaceutical composition produces a localized therapeutic effect; and wherein the therapeutic amount is effective to treat the cerebral vasospasm.

13. The method of claim 12, wherein the therapeutic agent comprises a transient receptor potential protein blocker.

14. The method of claim 12, wherein the therapeutic agent comprises an endothelin receptor antagonist.

15. The method of claim 12, wherein the carrier is a gel compound.

16. The method of claim 12, wherein the carrier is a semisolid compound.

17. The method of claim 12, wherein the carrier is a slow-release solid compound.

18. The method of claim 12, wherein the therapeutic agent is selected from the group consisting of amlodipine, aranidipine, azelnidipine, bamidipine, benidipine, bepridil, cinaldipine, diltiazem, efonidipine, felodipine, gallopamil, isradipine, lacidipine, lemildipine, lercanidipine, nicardipine, nifedipine, nilvadipine, nimodipine, nisoldipine, nitrendipine, manidipine, pranidipine, verapamil or a combination thereof.

19. The method of claim 12, wherein the therapeutic agent is selected from the group consisting of A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL 2500, PD-161721, RES 701-1, and RO 468443.

20. The method of claim 12, wherein the therapeutic agent is selected from the group consisting of SKF 96365 and LOE 908.

21. The method of claim 12, wherein the cistern closest to the cerebral artery in step (b) is from 0.001 mm to about 10 mm from the cerebral artery.

22. The method of claim 1, wherein the therapeutic agent further comprises at least one of a calcium channel antagonist, a, a transient receptor potential protein antagonist, or an endothelin receptor antagonist.

23. The method of claim 12, wherein the therapeutic agent further comprises at least one of a calcium channel antagonist, a, a transient receptor potential protein antagonist, or an endothelin receptor antagonist.

24. The method of claim 1, wherein the pharmaceutical carrier is a liquid pharmaceutical carrier, wherein the liquid pharmaceutical carrier transitions to a semisolid compound upon administration to the subarachnoid space.

25. The method of claim 12, wherein the pharmaceutical carrier is a liquid pharmaceutical carrier, wherein the liquid pharmaceutical carrier transitions to a semisolid compound upon administration to the subarachnoid space.

26. The method according claim 7, wherein the slow-release solid compound is a biodegradable polymer.

27. The method according to claim 26, wherein the biodegradable polymer is polylactide-polyglycolide.

28. The method according to claim 26, wherein the slow-release solid compound is a microencapsulated matrix.

29. The method according to claim 17, wherein the slow-release solid compound is a biodegradable polymer.

30. The method according to claim 29, wherein the biodegradable polymer is polylactide-polyglycolide.

31. The method according to claim 29, wherein the slow-release solid compound is a microencapsulated matrix.

32. The method according to claim 1, wherein the L-type voltage-gated calcium channel inhibitor is a dihydropyridine L-type calcium channel antagonist.

33. The method according to claim 1, wherein the L-type voltage-gated calcium channel inhibitor is nimodipine.

34. The method according to claim 12, wherein the L-type voltage-gated calcium channel inhibitor is a dihydropyridine L-type calcium channel antagonist.

35. The method according to claim 12, wherein the L-type voltage-gated calcium channel inhibitor is nimodipine.

36. The method according to claim 1, wherein the composition further comprises an R-type voltage-gated calcium channel inhibitor.

37. The method according to claim 12, wherein the composition further comprises an R-type voltage-gated calcium channel inhibitor.

* * * * *